(12) United States Patent  (10) Patent No.: US 11,033,175 B2
Watanabe  (45) Date of Patent: Jun. 15, 2021

(54) ENDOSCOPE SYSTEM AND OPERATION METHOD THEREFOR

(71) Applicant: FUJIFILM Corporation, Tokyo (JP)

(72) Inventor: Hiroki Watanabe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

(21) Appl. No.: 16/548,282

(22) Filed: Aug. 22, 2019

(65) Prior Publication Data

US 2019/0374088 A1   Dec. 12, 2019

Related U.S. Application Data

(63) Continuation of application No. PCT/JP2018/005789, filed on Feb. 19, 2018.

(30) Foreign Application Priority Data

Mar. 1, 2017  (JP) .............................. JP2017-038177

(51) Int. Cl.
*G06K 9/00* (2006.01)
*A61B 1/00* (2006.01)
(Continued)

(52) U.S. Cl.
CPC ........ *A61B 1/00009* (2013.01); *A61B 1/0052* (2013.01); *A61B 1/00055* (2013.01);
(Continued)

(58) Field of Classification Search
None
See application file for complete search history.

(56) References Cited

U.S. PATENT DOCUMENTS

2011/0254937 A1  10/2011  Yoshino
2012/0062717 A1   3/2012  Kinouchi et al.
(Continued)

FOREIGN PATENT DOCUMENTS

JP  2006-129950 A   5/2006
JP  2011-255006 A  12/2011
(Continued)

OTHER PUBLICATIONS

Extended European Search Report dated Feb. 24, 2020, issued in corresponding European Patent Application 18760990.4.
(Continued)

*Primary Examiner* — Atiba O Fitzpatrick
(74) *Attorney, Agent, or Firm* — Birch, Stewart, Kolasch & Birch, LLP

(57) ABSTRACT

Provided is an endoscope system capable of preventing a detection target from being overlooked in the case of using an automatic detection function for the detection target, and an operation method for the endoscope system. A comparison processing unit 74 performs comparison processing of comparing first-diagnosis identification information acquired at a first diagnosis with second-diagnosis identification information acquired at a second diagnosis that is different from the first diagnosis. A notification control unit 76 performs, if a determination is made that there is a difference in a detection target between the first diagnosis and the second diagnosis as a result of the comparison processing, control to make a notification about an oversight of the detection target.

20 Claims, 15 Drawing Sheets

(51) Int. Cl.
  *G06T 7/73* (2017.01)
  *A61B 1/005* (2006.01)
  *A61B 1/06* (2006.01)
  *G06T 7/00* (2017.01)

(52) U.S. Cl.
  CPC ...... *A61B 1/00059* (2013.01); *A61B 1/00188* (2013.01); *A61B 1/00195* (2013.01); *A61B 1/0646* (2013.01); *A61B 1/0684* (2013.01); *G06T 7/0014* (2013.01); *G06T 7/73* (2017.01); *G06T 2207/10068* (2013.01); *G06T 2207/30096* (2013.01)

(56) References Cited

U.S. PATENT DOCUMENTS

| | | | | |
|---|---|---|---|---|
| 2015/0254836 | A1* | 9/2015 | Sako | A61B 1/04 382/128 |
| 2016/0364862 | A1* | 12/2016 | Reicher | G06K 9/6269 |
| 2018/0098690 | A1 | 4/2018 | Iwaki | |
| 2019/0290371 | A1* | 9/2019 | Calef | A61B 34/30 |

FOREIGN PATENT DOCUMENTS

| | | |
|---|---|---|
| JP | 4861540 B2 | 1/2012 |
| JP | 2016-87370 A | 5/2016 |
| WO | WO 2016/199273 A1 | 12/2016 |

OTHER PUBLICATIONS

International Preliminary Report on Patentability and Written Opinion of the International Searching Authority (forms PCT/IB/337, PCT/ISA/237 and PCT/IB/326), dated Sep. 12, 2019, for corresponding International Application No. PCT/JP2018/005789, with a Written Opinion translation.

International Search Report (form PCT/ISA/210), dated Mar. 27, 2018, for corresponding International Application No. PCT/JP2018/005789, with an English translation.

Japanese Office Action dated Jul. 7, 2020, for corresponding Japanese Application No. 2019-502891, with English translation.

* cited by examiner

| POSITION INFORMATION COMPARISON PROCESSING | IMAGE FEATURE VALUE COMPARISON PROCESSING | DETERMINATION |
|---|---|---|
| MATCH | MATCH | THERE IS NO OVERSIGHT OF A DETECTION TARGET |
| MATCH | NOT MATCH | THERE IS AN OVERSIGHT OF A DETECTION TARGET AT THE SECOND DIAGNOSIS |
| NOT MATCH | NOT MATCH | THERE IS AN OVERSIGHT OF A DETECTION TARGET AT THE FIRST DIAGNOSIS |

ENDOSCOPE SYSTEM AND OPERATION METHOD THEREFOR

CROSS-REFERENCE TO RELATED APPLICATIONS

This application is a Continuation of PCT International Application No. PCT/JP2018/005789 filed on Feb. 19, 2018, which claims priority under 35 U.S.C § 119(a) to Japanese Patent Application No. 2017-038177 filed on Mar. 1, 2017. Each of the above application(s) is hereby expressly incorporated by reference, in its entirety, into the present application.

BACKGROUND OF THE INVENTION

1. Field of the Invention

The present invention relates to an endoscope system for automatically detecting a predetermined detection target, such as a lesion portion, by using image processing, and also relates to an operation method for the endoscope system.

2. Description of the Related Art

In the medical field, diagnoses using an endoscope system including a light source device, an endoscope, and a processor device have widely been performed. In the endoscope system, illumination light emitted by the light source device is applied to an observation target through an endoscope, and the processor device generates an image of the observation target on the basis of image signals acquired by imaging the observation target illuminated with the illumination light. The image is displayed on a monitor, and thereby a medical practitioner is able to make a diagnosis while viewing the image on the monitor.

When making an endoscopic diagnosis, a medical practitioner attempts to constantly detect all predetermined detection targets that are to be carefully observed, such as a lesion or benign tumor in an organ. However, the accuracy of detecting the detection targets is influenced by the experiences and skills of the medical practitioner and is also influenced by the degree of fatigue of the medical practitioner. Thus, to reduce variation in diagnostic accuracy among medical practitioners, a technique has been developed for analyzing, using a computer, a large amount of endoscopic data acquired in daily diagnoses and extracting information helpful in diagnoses. For example, an automatic detection function of automatically detecting a portion with a disease by a computer instead of a medical practitioner at an endoscopic diagnosis makes it possible to prevent a detection target from being overlooked by a medical practitioner, and is expected to increase the confidence of an endoscopic diagnosis.

Specifically, according to JP2016-87370A, a screen displayed in a magnifying endoscope for the large intestine is divided into a plurality of images, and automatic detection and diagnosis are performed using pattern recognition to determine which of five surface structure patterns that are clinically classified corresponds to each of the images. According to JP2006-129950A, a portion suspected to have a lesion is automatically detected in a capsule endoscope, and a notification is made using a sound or the like when such a portion is detected.

SUMMARY OF THE INVENTION

Detecting of a detection target using the above-described automatic detection function is based on the assumption that the detection target is included in an image. However, a situation is assumed where, when it is difficult to photograph the detection target, for example, when the detection target is hidden behind a fold, the detection target is not photographed and is not included in an image. If the detection target is not included in an image, the automatic detection function of the computer does not work, and the detection target to be originally detected will be overlooked.

An object of the present invention is to provide an endoscope system capable of preventing a detection target from being overlooked in the case of using an automatic detection function for the detection target, and an operation method for the endoscope system.

An endoscope system according to the present invention includes an identification information acquisition unit that acquires first-diagnosis identification information at a first diagnosis and acquires second-diagnosis identification information at a second diagnosis that is different from the first diagnosis; a comparison processing unit that performs comparison processing of comparing the first-diagnosis identification information with the second-diagnosis identification information; and a notification unit that makes, if a determination is made that there is a difference in a detection target between the first diagnosis and the second diagnosis as a result of the comparison processing, a notification about an oversight of the detection target.

Preferably, the first-diagnosis identification information includes an image feature value of a detection target at the first diagnosis detected from an image acquired at the first diagnosis, the second-diagnosis identification information includes an image feature value of a detection target at the second diagnosis detected from an image acquired at the second diagnosis, and the identification information acquisition unit has an image feature value detection unit that automatically detects the image feature value of the detection target at the first diagnosis and automatically detects the image feature value of the detection target at the second diagnosis.

Preferably, the first-diagnosis identification information includes an image feature value of a detection target at the first diagnosis detected from an image acquired at the first diagnosis, the second-diagnosis identification information includes an image feature value of a detection target at the second diagnosis detected from an image acquired at the second diagnosis, and the notification unit makes the notification about the oversight of the detection target if a determination is made that the image feature value of the detection target at the first diagnosis does not match the image feature value of the detection target at the second diagnosis as a result of the comparison processing.

Preferably, the first-diagnosis identification information includes an image feature value of a detection target at the first diagnosis detected from an image acquired at the first diagnosis, and position information at the first diagnosis, the second-diagnosis identification information includes an image feature value of the detection target at the second diagnosis detected from an image acquired at the second diagnosis, and position information at the second diagnosis, and the notification unit makes the notification about the oversight of the detection target if a determination is made that the position information at the first diagnosis matches the position information at the second diagnosis and that the image feature value of the detection target at the first diagnosis does not match the image feature value of the detection target at the second diagnosis as a result of the comparison processing.

Preferably, the notification unit makes the notification about the oversight of the detection target if a determination is made that position information at the first diagnosis does not match position information at the second diagnosis and that an image feature value of a detection target at the first diagnosis does not match an image feature value of the detection target at the second diagnosis as a result of the comparison processing.

Preferably, acquisition of identification information by the identification information acquisition unit is switched from acquisition of the first-diagnosis identification information to acquisition of the second-diagnosis identification information. Preferably, the notification unit makes the notification using a warning message. Preferably, the notification unit makes the notification using a warning sound.

Preferably, the endoscope system includes a plurality of light sources having different wavelength characteristics, and the image feature value detection unit detects, from an image acquired by using at least one of the plurality of light sources, the image feature value of the detection target at the first diagnosis or the image feature value of the detection target at the second diagnosis.

An operation method for an endoscope system of the present invention includes a step of acquiring, with an identification information acquisition unit, first-diagnosis identification information at a first diagnosis and second-diagnosis identification information at a second diagnosis that is different from the first diagnosis; a step of performing, with a comparison processing unit, comparison processing of comparing the first-diagnosis identification information with the second-diagnosis identification information; and a step of making, with a notification unit, if a determination is made that there is a difference in a detection target between the first diagnosis and the second diagnosis as a result of the comparison processing, a notification about an oversight of the detection target.

According to the present invention, it is possible to prevent a detection target from being overlooked in the case of using an automatic detection function for the detection target.

DESCRIPTION OF THE PREFERRED EMBODIMENTS

First Embodiment

Figure 1:
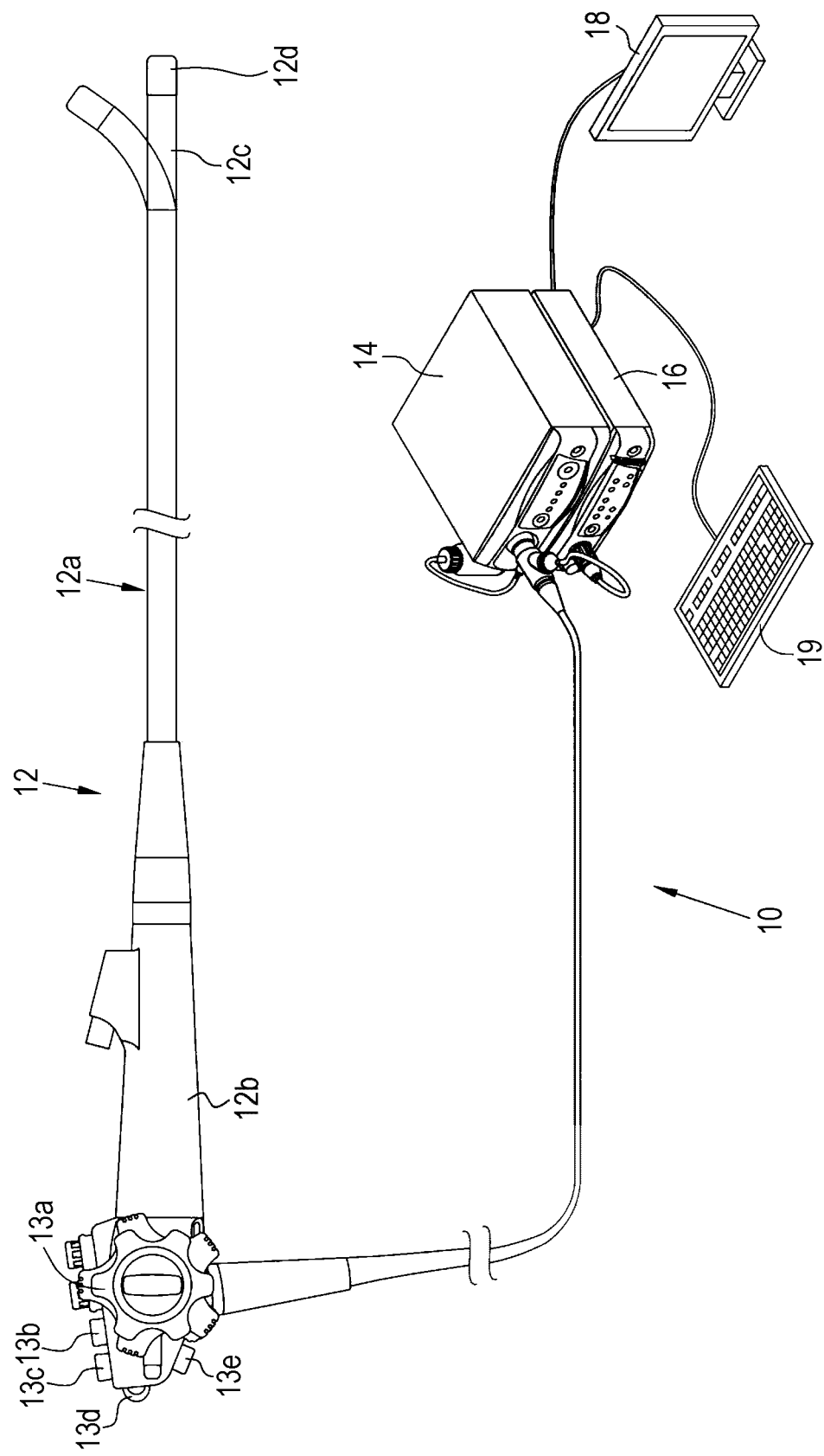
FIG. 1 is an external appearance view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14 and is electrically connected to the processor device 16. The endoscope 12 has an insertion section 12a to be inserted into a subject, an operation section 12b provided at a base end portion of the insertion section 12a, and a bending portion 12c and a distal end portion 12d that are provided on a distal end side of the insertion section 12a. Operating an angle knob 13a of the operation section 12b causes the bending portion 12c to perform a bending operation. The bending operation causes the distal end portion 12d to be directed in a desired direction.

The operation section 12b is provided with a still image acquisition unit 13b used for an operation of acquiring a still image, a mode switching unit 13c used for an operation of switching an observation mode, a zoom operation unit 13d used for an operation of changing zoom magnification, and an identification information switching unit 13e, in addition to the angle knob 13a. The still image acquisition unit 13b is capable of performing a freeze operation of displaying a still image of an observation target on the monitor 18 and a release operation of storing a still image in storage.

The endoscope system 10 has a normal mode, a special mode, and a detection-target-oversight-prevention mode as observation modes. When the observation mode is the normal mode, normal light generated by combining light beams of a plurality of colors at a light amount ratio Lc for the normal mode is emitted, and a normal image is displayed on the monitor 18 on the basis of image signals acquired by imaging an observation target illuminated with the normal light. When the observation mode is the special mode, special light generated by combining light beams of a plurality of colors at a light amount ratio Ls for the special mode is emitted, and a special image is displayed on the monitor 18 on the basis of image signals acquired by imaging an observation target illuminated with the special light.

When the observation mode is the detection-target-oversight-prevention mode, normal light and special light are alternately emitted. A normal image acquired by imaging an observation target illuminated with the normal light is displayed as a main display image on the monitor 18, and a special image acquired by imaging the observation target illuminated with the special light is displayed as a sub display image on the monitor 18. In the detection-target-oversight-prevention mode, whether there is an oversight of a detection target is determined, and a determination result is displayed in the main display image or the sub display image. Showing or hiding of the main display image and showing or hiding of the sub display image can be set as necessary.

The processor device 16 is electrically connected to the monitor 18 and the console 19. The monitor 18 outputs and displays an image of an observation target, information accompanying the image, and so forth. The console 19 functions as a user interface that receives an input operation of designating a region of interest (ROI), setting a function, or the like.

Figure 2:
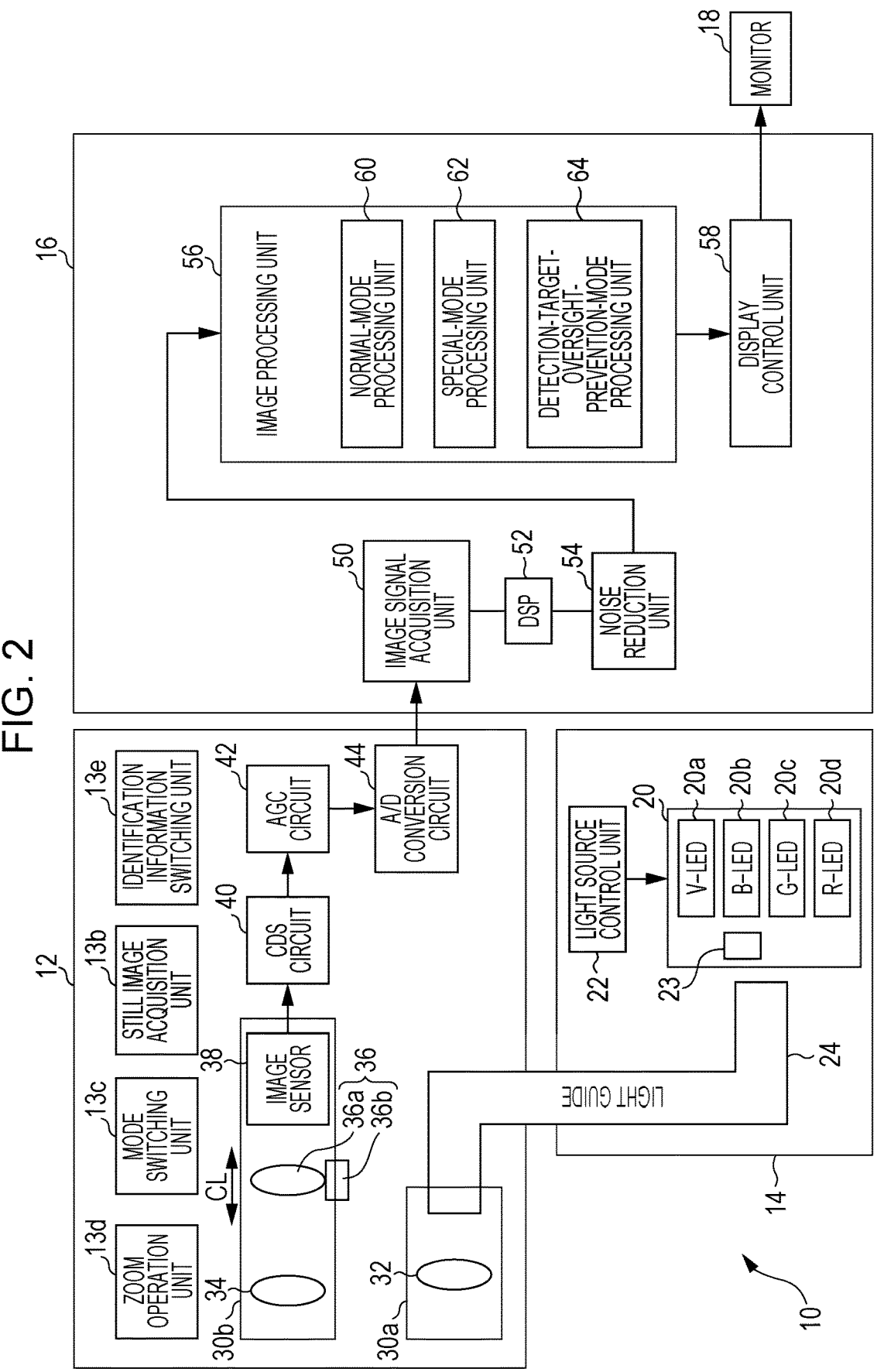
FIG. 2 is a block diagram illustrating the functions of the endoscope system according to a first embodiment.

As illustrated in FIG. 2, the light source device 14 includes a light source unit 20 that emits illumination light used to illuminate an observation target, and a light source control unit 22 that controls the light source unit 20. The light source unit 20 is a semiconductor light source, such as light emitting diodes of a plurality of colors. The light source control unit 22 turns ON/OFF the LEDs or the like and adjusts driving currents and driving voltages for the LEDs or the like, thereby controlling the amount of illumination light to be emitted. In addition, the light source control unit 22 controls the wavelength range of the illumination light by, for example, changing an optical filter.

Figure 3:
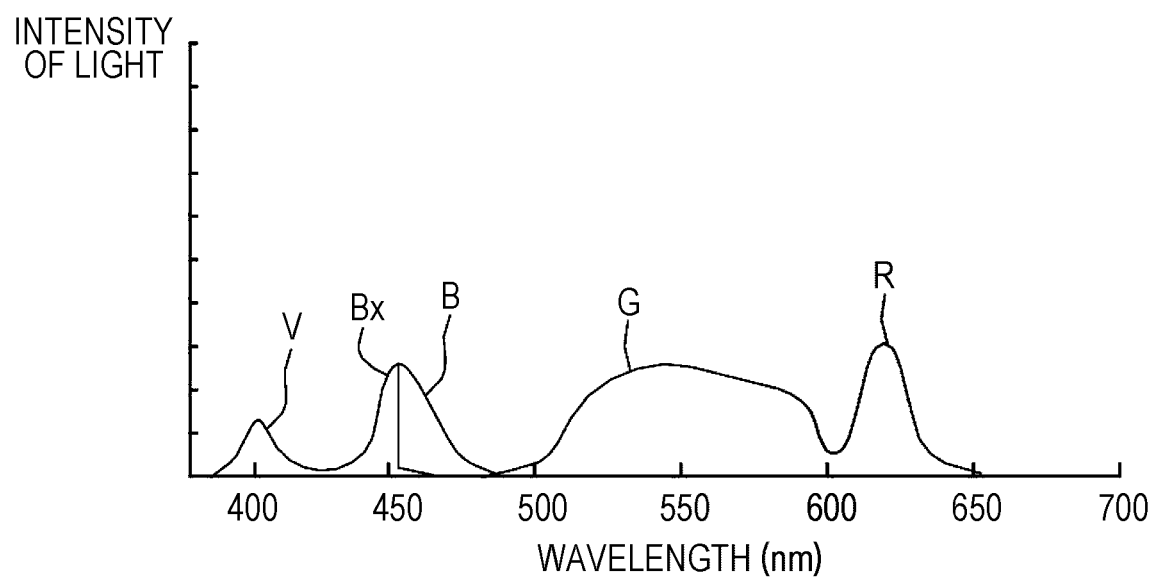
FIG. 3 is a graph illustrating a spectrum of violet light V, blue light B, blue light Bx, green light G, and red light R.

In the first embodiment, the light source unit 20 has LEDs of four colors: a violet light emitting diode (V-LED) 20a, a blue light emitting diode (B-LED) 20b, a green light emitting diode (G-LED) 20c, and a red light emitting diode (R-LED) 20d, and a wavelength cut filter 23. As illustrated in FIG. 3, the V-LED 20a emits violet light V in a wavelength range of 380 nm to 420 nm.

The B-LED 20b emits blue light B in a wavelength range of 420 nm to 500 nm. Of the blue light B emitted by the B-LED 20b, at least the long-wavelength side relative to a peak wavelength of 460 nm is cut off by the wavelength cut filter 23. Accordingly, blue light Bx that has passed through the wavelength cut filter 23 is in a wavelength range of 420 nm to 460 nm. The light in the wavelength range on the long-wavelength side relative to 460 nm is cut off because the light in the wavelength range on the long-wavelength side relative to 460 nm is a factor in decreasing the contrast of blood vessels as an observation target. The wavelength cut filter 23 may decrease the amount of light in the wavelength range on the long-wavelength side relative to 460 nm instead of cutting off the light in the wavelength range on the long-wavelength side relative to 460 nm.

The G-LED 20c emits green light G in a wavelength range of 480 nm to 600 nm. The R-LED 20d emits red light R in a wavelength range of 600 nm to 650 nm. The light emitted by each of the LEDs 20a to 20d may have a center wavelength and a peak wavelength that are identical to or different from each other.

The light source control unit 22 controls ON/OFF of each of the LEDs 20a to 20d and the amount of light emission in an ON state independently from each other, thereby adjusting the emission timing, emission period, amount of light, and spectrum of illumination light. The ON/OFF control by the light source control unit 22 varies according to an observation mode. A reference brightness can be set by a brightness setting unit of the light source device 14, the console 19, or the like.

Figure 4:
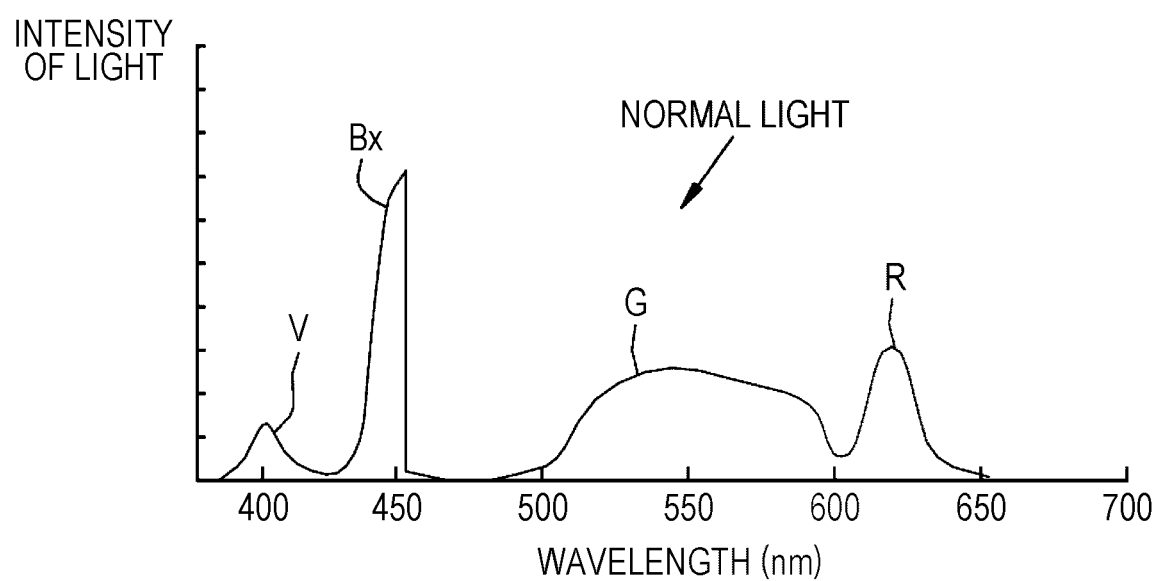
FIG. 4 is a graph illustrating a spectrum of normal light according to the first embodiment.

In the normal mode, the light source control unit 22 turns on all of the V-LED 20a, the B-LED 20b, the G-LED 20c, and the R-LED 20d. At this time, as illustrated in FIG. 4, the light amount ratio Lc among the violet light V, the blue light Bx, the green light G, and the red light R is set such that the peak intensity of the blue light Bx is higher than the peak intensities of the violet light V, the green light G, and the red light R. Accordingly, in the normal mode, the light source device 14 emits, as normal light, multicolor light for the normal mode including the violet light V, the blue light Bx, the green light G, and the red light R. The normal light has a certain intensity or more in the blue range to the red range and is thus substantially white.

Figure 5:
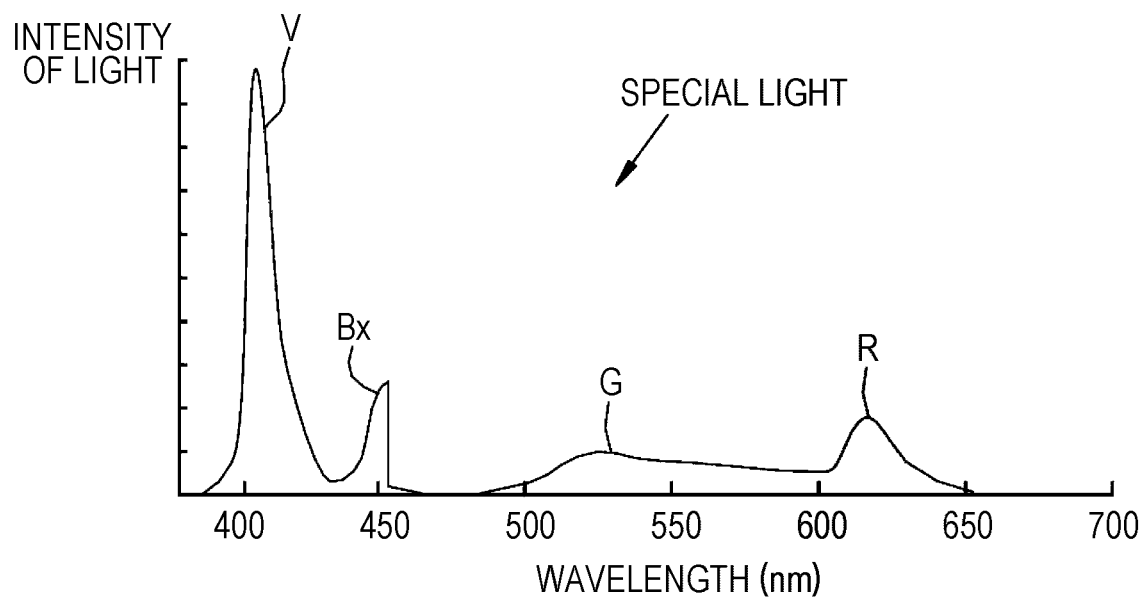
FIG. 5 is a graph illustrating a spectrum of special light according to the first embodiment.

In the special mode, the light source control unit 22 turns on all of the V-LED 20a, the B-LED 20b, the G-LED 20c, and the R-LED 20d. At this time, as illustrated in FIG. 5, the light amount ratio Ls among the violet light V, the blue light Bx, the green light G, and the red light R is set such that the peak intensity of the violet light V is higher than the peak intensities of the blue light Bx, the green light G, and the red light R and such that the peak intensities of the green light G and the red light R are lower than the peak intensities of the violet light V and the blue light Bx. Accordingly, in the special mode, the light source device 14 emits, as special light, multicolor light for the special mode including the violet light V, the blue light Bx, the green light G, and the red light R. The special light has a large proportion of the violet light V and is thus bluish. The special light does not need to include light of all the four colors, and may include light from at least one of the LEDs 20a to 20d of four colors.

In the detection-target-oversight-prevention mode, the light source control unit 22 controls the V-LED 20a, the B-LED 20b, the G-LED 20c, and the R-LED 20d so that normal light and special light are alternately emitted on a frame by frame basis. That is, the light source control unit 22 performs control to alternately switch the light amount ratio among the violet light V, the blue light Bx, the green light G, and the red light R between the light amount ratio Lc and the light amount ratio Ls on a frame by frame basis.

As illustrated in FIG. 2, the illumination light emitted by the light source unit 20 passes through a light path coupling unit (not illustrated) formed of a mirror, a lens, and the like and then enters a light guide 24 that is in the insertion section 12a. The light guide 24 is built in the endoscope 12 and a universal cord, and causes the illumination light to propagate to the distal end portion 12d of the endoscope 12. The universal cord is a cord that connects the endoscope 12 to the light source device 14 and the processor device 16. A multimode fiber may be used as the light guide 24. As an example, a small-diameter fiber cable with a core diameter of 105 μm, a clad diameter of 125 μm, and a diameter including a protective layer serving as an outer cover of ϕ0.3 mm to ϕ0.5 mm may be used as the light guide 24.

The distal end portion 12d of the endoscope 12 is provided with an illumination optical system 30a and an imaging optical system 30b. The illumination optical system 30a has an illumination lens 32. An observation target is illuminated, via the illumination lens 32, with illumination light that has propagated through the light guide 24. The imaging optical system 30b has an objective lens 34, a magnifying optical system 36, and an image sensor 38. Various types of light, such as reflected light, scattered light, and fluorescence from the observation target, enters the image sensor 38 through the objective lens 34 and the magnifying optical system 36. Accordingly, an image of the observation target is formed on the image sensor 38.

The magnifying optical system 36 includes a zoom lens 36a that magnifies an observation target, and a lens driving unit 36b that moves the zoom lens 36a in optical-axis directions CL. The zoom lens 36a is freely moved between a telephoto end and a wide end in accordance with zoom control by the lens driving unit 36b, thereby magnifying or demagnifying the image of the observation target formed on the image sensor 38.

The image sensor 38 is a color image sensor that performs imaging of an observation target irradiated with illumination light. Each pixel of the image sensor 38 is provided with a red (R) color filter, a green (G) color filter, or a blue (B) color filter. The image sensor 38 receives violet to blue light in a B pixel provided with the B color filter, receives green light in a G pixel provided with the G color filter, and receives red light in an R pixel provided with the R color filter. Also, the image sensor 38 outputs image signals of individual colors of RGB from the pixels of the individual colors. The image sensor 38 transmits the output image signals to a CDS circuit 40.

In the normal mode, the image sensor 38 performs imaging of an observation target illuminated with normal light, thereby outputting a Bc image signal from the B pixel, outputting a Gc image signal from the G pixel, and outputting an Rc image signal from the R pixel. In the special mode, the image sensor 38 performs imaging of an observation target illuminated with special light, thereby outputting a Bs image signal from the B pixel, outputting a Gs image signal from the G pixel, and outputting an Rs image signal from the R pixel. In the detection-target-oversight-prevention mode, the image sensor 38 outputs a Bc image signal, a Gc image signal, and an Rc image signal from the B pixel, the G pixel, and the R pixel, respectively, when performing imaging of an observation target illuminated with normal light, and outputs a Bs image signal, a Gs image signal, and an Rs image signal from the B pixel, the G pixel, and the R pixel, respectively, when performing imaging of the observation target illuminated with special light.

A charge coupled device (CCD) image sensor, a complementary metal-oxide semiconductor (CMOS) image sensor, or the like can be used as the image sensor 38. Instead of the image sensor 38 provided with color filters of the primary colors RGB, a complementary-color image sensor including complementary-color filters of cyan (C), magenta (M), yellow (Y), and green (G) may be used. In the case of using the complementary-color image sensor, image signals of four colors CMYG are output. Thus, by converting image signals of four colors CMYG into image signals of three colors RGB by using complementary color to primary color conversion, image signals of individual colors RGB similar to those in the image sensor 38 can be acquired. Alternatively, a monochrome sensor not provided with color filters may be used instead of the image sensor 38.

The CDS circuit 40 performs correlated double sampling (CDS) on analog image signals received from the image sensor 38. The image signals output from the CDS circuit 40 are input to an AGC circuit 42. The AGC circuit 42 performs automatic gain control (AGC) on the image signals input thereto. An analog to digital (A/D) conversion circuit 44 converts the analog image signals output from the AGC circuit 42 into digital image signals. The A/D conversion circuit 44 inputs the digital image signals generated through the A/D conversion to the processor device 16.

Figure 6:
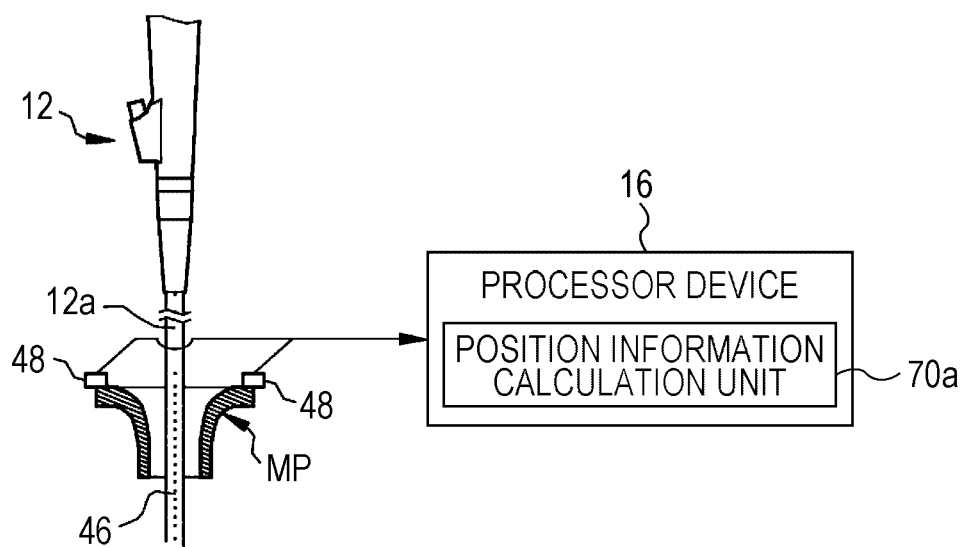
FIG. 6 is an explanatory diagram illustrating a method for calculating position information.

As illustrated in FIG. 6, measuring graduations 46 for measuring an insertion length of the insertion section 12a in a body are marked on an outer surface of the insertion section 12a of the endoscope 12. The measuring graduations 46 are constituted by points marked at a predetermined interval (for example, an interval of 1 cm) in the longitudinal direction of the insertion section 12a. The measuring graduations 46 are detected by a graduation detection sensor 48 provided near the mouth (in the case of upper endoscopy) or the anus (in the case of lower endoscopy) of a patient. The graduation detection sensor 48 is connected to the processor device 16 in a wired or wireless manner, and information detected by the graduation detection sensor 48 is transmitted to the processor device 16. A position information calculation unit 70a of the processor device 16 calculates position information about the insertion section 12a in a body cavity on the basis of a detection result obtained by the graduation detection sensor 48.

FIG. 6 illustrates that the graduation detection sensor 48 is provided on a mouthpiece MP held by the mouth of a patient. Here, position information is calculated by using the measuring graduations 46 and the graduation detection sensor 48. Alternatively, a magnetic sensor (not illustrated) may be provided at the distal end portion 12d of the insertion section 12a, and position information may be calculated by the position information calculation unit 70a on the basis of information acquired by the magnetic sensor.

As illustrated in FIG. 2, the processor device 16 includes an image signal acquisition unit 50, a digital signal processor (DSP) 52, a noise reduction unit 54, an image processing unit 56, and a display control unit 58.

The image signal acquisition unit 50 acquires digital image signals corresponding to an observation mode from the endoscope 12. In the normal mode, the image signal acquisition unit 50 acquires a Bc image signal, a Gc image signal, and an Rc image signal. In the special mode, the image signal acquisition unit 50 acquires a Bs image signal, a Gs image signal, and an Rs image signal. In the detection-target-oversight-prevention mode, the image signal acquisition unit 50 acquires a Bc image signal, a Gc image signal, and an Rc image signal of one frame during illumination with normal light, and acquires a Bs image signal, a Gs image signal, and an Rs image signal of one frame during illumination with special light.

The DSP 52 performs various signal processing operations, such as defect correction processing, offset processing, DSP gain correction processing, linear matrix processing, gamma conversion processing, and demosaicing processing, on the image signals acquired by the image signal acquisition unit 50. The defect correction processing corrects a signal of a defective pixel of the image sensor 38. The offset processing removes a dark current component from the image signal that has been subjected to the defect correction processing and sets an accurate zero level. The DSP gain correction processing multiplies the image signal that has been subjected to the offset processing by a specific DSP gain, thereby adjusting the signal level.

The linear matrix processing increases the color reproducibility of the image signal that has been subjected to the DSP gain correction processing. The gamma conversion processing adjusts the brightness and chroma of the image signal that has been subjected to the linear matrix processing. The image signal that has been subjected to the gamma conversion processing is subjected to demosaicing processing (also referred to as isotropic processing or synchronization processing), thereby generating, through interpolation, a signal of color insufficient in each pixel. The demosaicing processing enables all pixels to have signals of individual colors RGB. The noise reduction unit 54 performs noise reduction processing using, for example, a moving-average method, a median filter method, or the like, on the image signal that has been subjected to the demosaicing processing and so forth in the DSP 52, thereby reducing noise. The image signal that has been subjected to the noise reduction is input to the image processing unit 56.

The image processing unit 56 includes a normal-mode processing unit 60, a special-mode processing unit 62, and a detection-target-oversight-prevention-mode processing unit 64. The normal-mode processing unit 60 operates when the normal mode is set, and performs color conversion processing, color enhancement processing, and structure enhancement processing on the Bc image signal, Gc image signal, and Rc image signal that have been received. In the color conversion processing, color conversion processing is performed on the RGB image signals by using 3×3 matrix processing, gradation transformation processing, three-dimensional look up table (LUT) processing, and the like.

The color enhancement processing is performed on the RGB image signals that have been subjected to color conversion processing. The structure enhancement processing is processing of enhancing the structure of an observation target and is performed on the RGB image signals that have been subjected to the color enhancement processing. The above-described various image processing operations enable a normal image to be acquired. The normal image is an image acquired on the basis of normal light including the violet light V, the blue light Bx, the green light G, and the red light R with a well-balanced ratio, and is thus an image with natural colors. The normal image is input to the display control unit 58.

The special-mode processing unit 62 operates when the special mode is set. The special-mode processing unit 62 performs color conversion processing, color enhancement processing, and structure enhancement processing on the Bs image signal, Gs image signal, and Rs image signal that have been received. The processing performed in the color conversion processing, the color enhancement processing, and the structure enhancement processing is similar to that in the normal-mode processing unit 60. The above-described various image processing operations enable a special image to be acquired. The special image is an image acquired on the basis of special light in which the amount of the violet light V having a high hemoglobin absorption coefficient of blood vessels is larger than the amount of the blue light Bx, the green light G, and the red light R, and thus the resolution of a blood vessel structure and a gland duct structure is higher than that of other structures. The special image is input to the display control unit 58.

The detection-target-oversight-prevention-mode processing unit 64 operates when the detection-target-oversight-prevention mode is set. The detection-target-oversight-prevention-mode processing unit 64 automatically performs processing of detecting an image feature value from an image based on the Bs image signal, Gs image signal, and Rs image signal that have been received, and also performs processing of acquiring position information in a lumen. The image feature value and the position information correspond to identification information that is used to detect a detection target. The identification information includes first-diagnosis identification information acquired at a first diagnosis and second-diagnosis identification information acquired at a second diagnosis that is different from the first diagnosis. A switching operation for determining which of the first-diagnosis identification information and the second-diagnosis identification information is to be acquired is performed by the identification information switching unit 13e.

The detection-target-oversight-prevention-mode processing unit 64 performs comparison processing of comparing the first-diagnosis identification information with the second-diagnosis identification information, and makes, if a determination is made that there is an oversight of a detection target at the first diagnosis and the second diagnosis as a result of the comparison processing, a notification about the fact. In addition, the detection-target-oversight-prevention-mode processing unit 64 generates a main display image from a Bc image signal, a Gc image signal, and an Rc image signal, and generates a sub display image from a Bs image signal, a Gs image signal, and an Rs image signal. The details of the detection-target-oversight-prevention-mode processing unit 64 will be described below.

The display control unit 58 performs display control for displaying an image and data received from the image processing unit 56 on the monitor 18. When the normal mode is set, the display control unit 58 performs control to display a normal image on the monitor 18. When the special mode is set, the display control unit 58 performs control to display a special image on the monitor 18. When the detection-target-oversight-prevention mode is set, the display control unit 58 performs control to display a main display image or a sub display image on the monitor 18, and also performs control to display a main display image or sub display image including guidance about an oversight of a detection target on the monitor 18 or to output a sound from the monitor 18.

Figures 7, 8:
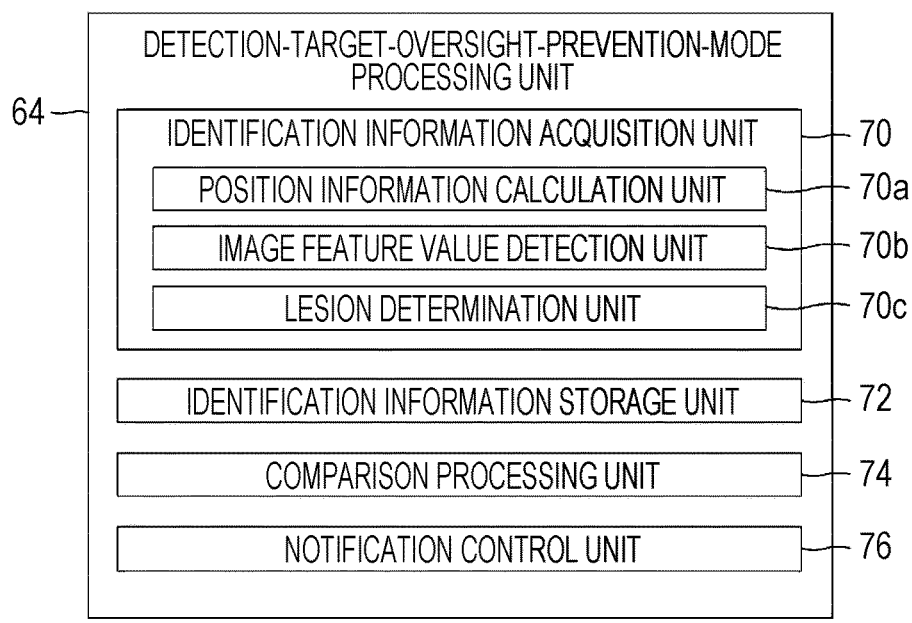
FIG. 7 is a block diagram illustrating the functions of a detection-target-oversight-prevention-mode processing unit.
FIG. 8 is a table illustrating determinations based on results of comparison processing.

As illustrated in FIG. 7, the detection-target-oversight-prevention-mode processing unit 64 includes an identification information acquisition unit 70, an identification information storage unit 72, a comparison processing unit 74, and a notification control unit 76. The identification information acquisition unit 70 includes the position information calculation unit 70a that calculates position information on the basis of a detection result obtained by the graduation detection sensor 48, an image feature value detection unit 70b that automatically detects an image feature value from at least one of the Bs image signal, the Gs image signal, or the Rs image signal, and a lesion determination unit 70c that determines whether or not the detected image feature value corresponds to an image feature value specific to a detection target. The lesion determination unit 70c stores in advance a plurality of template image feature values of detection targets as image information specific to the detection targets, for example, and determines, using artificial intelligence (AI) or the like, whether or not an extracted image feature value matches a template image feature value. Here, "match" includes a case where the image feature values compared with each other match and a case where the difference between the image feature values compared with each other is within a certain range.

When "acquisition of first-diagnosis identification information" is set by the identification information switching unit 13e and the lesion determination unit 70c determines that the detected image feature value corresponds to the image feature value specific to a detection target, the identification information acquisition unit 70 stores the image feature value and the position information at the point of time as first-diagnosis identification information in the identification information storage unit 72.

On the other hand, when "acquisition of second-diagnosis identification information" is set by the identification information switching unit 13e and the lesion determination unit 70c determines that the detected image feature value does not correspond to the image feature value specific to a detection target, every time the position information calculation unit 70a calculates position information, the identification information acquisition unit 70 transmits the calculated position information as second-diagnosis identification information to the comparison processing unit 74. When "acquisition of second-diagnosis identification information" is set by the identification information switching unit 13e and the lesion determination unit 70c determines that the detected image feature value corresponds to the image feature value specific to a detection target, the identification information acquisition unit 70 transmits the image feature value and the position information at the point of time as second-diagnosis identification information to the comparison processing unit 74.

When "acquisition of second-diagnosis identification information" is set by the identification information switching unit 13e, the comparison processing unit 74 performs comparison processing of comparing the first-diagnosis identification information stored in the identification information storage unit 72 with the second-diagnosis identification information. In the comparison processing, two processing operations are performed: position information comparison processing of comparing the position information at the first diagnosis included in the first-diagnosis identification information with the position information at the second diagnosis included in the second-diagnosis identification information; and image feature value comparison processing of comparing the image feature value at the first diagnosis included in the first-diagnosis identification information with the image feature value at the second diagnosis included in the second-diagnosis identification information.

As illustrated in FIG. 8, if the position information at the first diagnosis matches the position information at the second diagnosis in the position information comparison processing and if the image feature value at the first diagnosis matches the image feature value at the second diagnosis in the image feature value comparison processing, a determination "there is no oversight of a detection target" is made. On the other hand, if the position information at the first diagnosis matches the position information at the second diagnosis in the position information comparison processing and if the image feature value at the first diagnosis does not match the image feature value at the second diagnosis in the image feature value comparison processing, a determination "there is an oversight of a detection target at the second diagnosis" is made. "The image feature values match" includes a case where the image feature values compared with each other match and a case where the difference between the image feature values compared with each other is within a certain range. "The pieces of position information match" includes a case where the positions compared with each other match and a case where the difference between the positions compared with each other is within a certain range.

If the position information at the first diagnosis does not match the position information at the second diagnosis in the position information comparison processing and if the image feature value at the first diagnosis does not match the image feature value at the second diagnosis in the image feature value comparison processing, a determination "there is an oversight of a detection target at the first diagnosis" is made.

Figure 9:
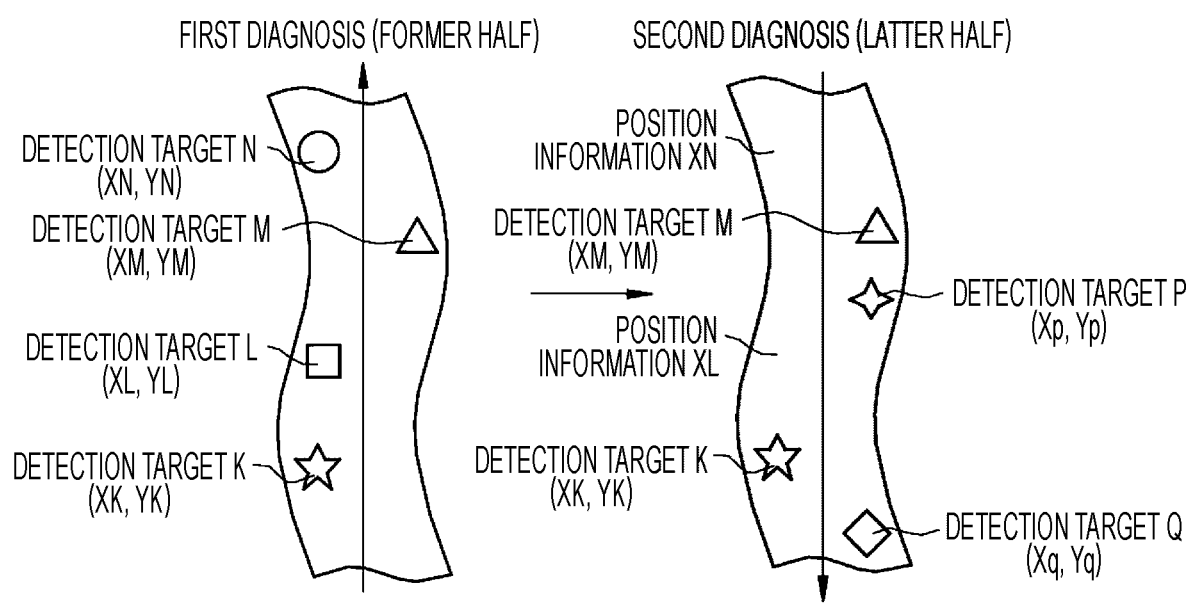
FIG. 9 is an explanatory diagram illustrating a specific example of comparison processing.

Referring to FIG. 9, a description will be given of a specific example of comparison processing in a case where the insertion section 12a of the endoscope 12 goes and returns along the same path in a lumen of the stomach, esophagus, large intestine, or the like, and where the former half corresponds to a first diagnosis and the latter half corresponds to a second diagnosis. At the first diagnosis in the former half, the identification information switching unit 13e sets "acquisition of first-diagnosis identification information". At the first diagnosis in the former half, for example, the identification information acquisition unit 70 acquires pieces of identification information of four detection targets: a detection target K, a detection target L, a detection target M, and a detection target N, and stores the pieces of identification information in the identification information storage unit 72. Here, the detection target K has position information XK and an image feature value YK as first-diagnosis identification information. The detection target L has position information XL and an image feature value YL as first-diagnosis identification information. The detection target M has position information XM and an image feature value YM as first-diagnosis identification information. The detection target N has position information XN and an image feature value YN as first-diagnosis identification information.

When the distal end portion 12d of the insertion section 12a reaches the terminal of the former half, the identification information switching unit 13e is operated, and the identification information switching unit 13e performs switching to "acquisition of second-diagnosis identification information". Subsequently, at the second diagnosis in the latter half, the distal end portion 12d of the insertion section 12a is caused to return along the same path as the former half. At the second diagnosis, the comparison processing unit 74 performs comparison processing of comparing the first-diagnosis identification information with the second-diagnosis identification information not only when the identification information acquisition unit 70 detects an image feature value of a detection target but also every time the position information calculation unit 70a calculates position information.

For example, when the position information XM is acquired at the second diagnosis in the latter half and the image feature value YM of the detection target M is detected at the position, both the pieces of position information XM and the image feature values YM acquired at the first diagnosis and the second diagnosis match in the comparison processing. In this case, a determination "there is no oversight of a detection target" is made. Similarly, when the position information XK is acquired at the second diagnosis in the latter half and the image feature value YK of the detection target K is detected at the position, a determination "there is no oversight of a detection target" is made.

On the other hand, when the position information XN is acquired at the second diagnosis in the latter half and the image feature value of the detection target N is not detected at the position, the pieces of position information match but the image feature values do not match in the comparison processing. In this case, the detection target N detected at the first diagnosis is overlooked at the second diagnosis, and thus a determination "there is an oversight of a detection target at the second diagnosis" is made. When the position information XL is acquired at the second diagnosis in the latter half and the image feature value of the detection target L is not detected at the position, the detection target L detected at the first diagnosis is overlooked at the second diagnosis, and thus a determination "there is an oversight of a detection target at the second diagnosis" is made.

When position information Xp is acquired at the second diagnosis in the latter half and an image feature value Yp of a detection target P is detected at the position, none of the position information and the image feature value do not match in the comparison processing. In this case, the detection target P is overlooked at the first diagnosis, and thus a determination "there is an oversight of a detection target at the first diagnosis" is made. When position information Xq is acquired at the second diagnosis in the latter half and an image feature value Yq of a detection target Q is detected at the position, the detection target Q is overlooked at the first diagnosis, and thus a determination "there is an oversight of a detection target at the first diagnosis" is made.

Figure 10:
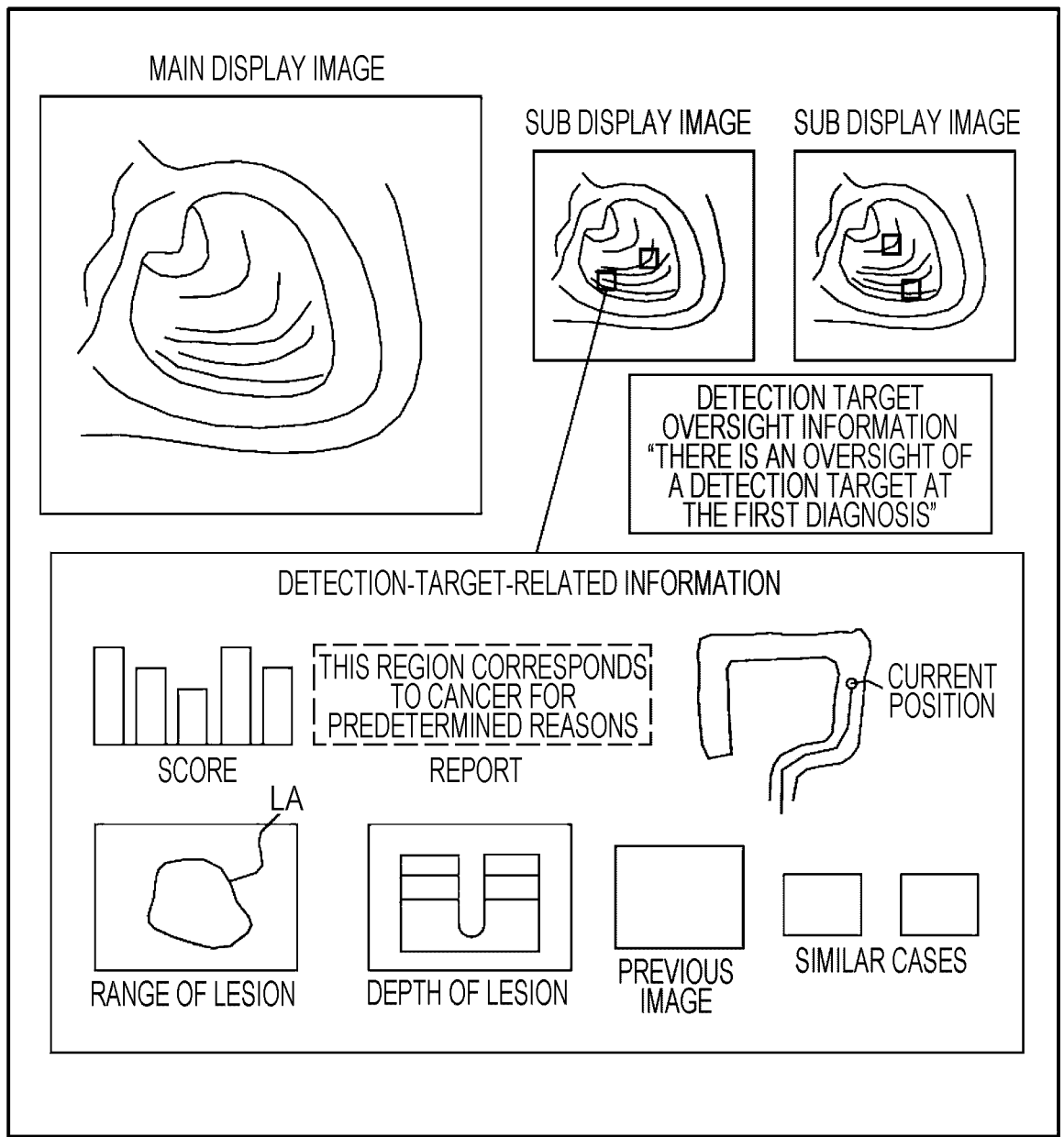
FIG. 10 is an image diagram of a monitor that displays a main display image, sub display images, and detection-target-related information.

The notification control unit 76 performs, via the display control unit 58, control to make a notification about information related to a detection target, such as detection of the detection target or an oversight of the detection target. The notification control unit 76 generates a main display image from a Bc image signal, a Gc image signal, and an Rc image signal, and also generates a sub display image from a Bs image signal, a Gs image signal, and an Rs image signal. The generated main display image and sub display image are displayed on the monitor 18 via the display control unit 58 as illustrated in FIG. 10. In FIG. 10, the main display image is displayed in a larger size than the sub display images, but the sub display images may be displayed in a larger size than the main display image. Alternatively, either the main display image or the sub display images may be displayed. Although two sub display images are displayed side by side here, one sub display image or three or more sub display images may be displayed.

When the lesion determination unit 70c detects an image feature value of a detection target, the notification control unit 76 performs control to display an indicator, such as a square, circle, or arrow (in FIG. 10, squares are displayed as indicators) at the position of the detection target in the sub display image in a superimposed manner. This enables a user to recognize the position of the detection target. The indicator may be displayed on the main display image in a superimposed manner instead of or in addition to the sub display image. Alternatively, a warning sound for giving a notification indicating that the detection target has been detected may be output from a speaker of the monitor 18 instead of or in addition to the indicator.

The indicator may be displayed not only on a still image but also on a moving image. In that case, the indicator may be displayed to automatically follow a moving lesion on the basis of an image feature of the lesion that has once been detected. Furthermore, when a coloring agent of various types, such as indigo carmine or methylene blue, is applied to facilitate diagnosis, it is preferable to perform automatic detection on the basis of the surface structure or blood vessel structure of a predetermined detection target and to perform display using an indicator, although color information of an original lesion is lost. When a detection target such as a lesion is detected, a still image of the detection target may be automatically captured at each time and may be automatically stored as log information.

When the comparison processing unit 74 makes a determination "there is an oversight of a detection target at the first diagnosis" or "there is an oversight of a detection target at the second diagnosis", the notification control unit 76 performs control to display the determination result as a warning message on the monitor 18. In FIG. 10, "there is an oversight of a detection target at the first diagnosis" is displayed as a warning message. When a determination "there is no oversight of a detection target" is made, the notification control unit 76 may display guidance indicating the determination on the monitor 18. The "notification unit" of the present invention corresponds to a configuration including at least the notification control unit 76 and the monitor 18 (display unit).

When the lesion determination unit 70c detects an image feature value of a detection target, the notification control unit 76 also displays information related to the detection target. The information related to the detection target is displayed in association with an indicator attached to the detection target by using a line or the like. Preferably, when a detection target is detected, a region including the detection target and a surrounding region is automatically magnified by electronic zoom, and the magnified image of the region is displayed as the information related to the detection target. It is also preferable to display a differentiation result of the detection target, such as a total score evaluating a probability of being a lesion region or a parameter score used to calculate the total score. As the total score, for example, a malignancy grade or stage of cancer may be displayed. As the parameter score, for example, the regularity of the pattern of blood vessels in the surface of cancer, or the regularity of the uneven pattern on the surface may be displayed.

Preferably, the differentiation result of the detection target is acquired by using artificial intelligence (AI) on the basis of the image feature value of the detection target. When a medical practitioner observes the detection target, such as a lesion, from a certain distance or at a certain magnification ratio using electronic zoom to perform differentiation, the light source mode may be automatically switched to the mode enabling easy differentiation, for example, to the special mode when the medical practitioner reaches a position at the certain distance or when the certain magnification ratio is reached in zooming.

Preferably, the range of the detection target is detected and the range of the detected lesion may be displayed as information related to the detection target by using a contour line LA such as a curve. Preferably, when it is determined that the detection target needs to be observed with special care because the total score or parameter score thereof acquired as a result of differentiation is greater than or equal to a certain value, the detection target is displayed with a predetermined region including the detection target being surrounded by a yellow or red indicator or the like so that particular attention is paid to the lesion. When a single detection target includes regions having different properties, the scores of the individual regions may be displayed by assigning total scores or parameter scores to a color map, or total scores or parameter scores may be displayed for the individual regions. Preferably, the depth of the detection target is detected and the detected depth of the detection target is displayed as information related to the detection target. Also, a subjective report related to the detection target may be displayed as information related to the detection target (for example, "this region corresponds to cancer for predetermined reasons").

The above-described differentiation using AI or the like does not necessarily guarantee 100% accurate differentiation of a lesion. Thus, the confidence of the differentiation result may be displayed, or an "agreement button" for asking a medical practitioner whether or not he/she agrees to the differentiation result may be displayed on the monitor 18, so that the medical practitioner is allowed to give final approval for the differentiation result. In this case, the "agreement button" is preferably operated by using the console 19.

With use of the position information calculated by the position information calculation unit 70a, a detection position of a detection target in a lumen or a current position of the distal end portion 12d of the endoscope 12 may be displayed as information related to the detection target. In FIG. 10, a detection position of a detection target in the entire large intestine and a current position of the distal end portion 12d are displayed. In addition, a previous image of the detection target detected in the former half or at a previous diagnosis, or one or a plurality of images of cases similar to the detected detection target may be displayed as information related to the detection target.

Preferably, various pieces of information illustrated in FIG. 10, such as an image, total score, parameter score, report, and detection position of a detection target such as a lesion, are automatically stored as a log. Furthermore, when retrieving and using various pieces of information previously recorded as a log, such as an image of a similar case or a previous image, during an examination, recognition means such as machine learning or AI may be used as means for identifying the image of a similar case or the previous image.

Figure 11:
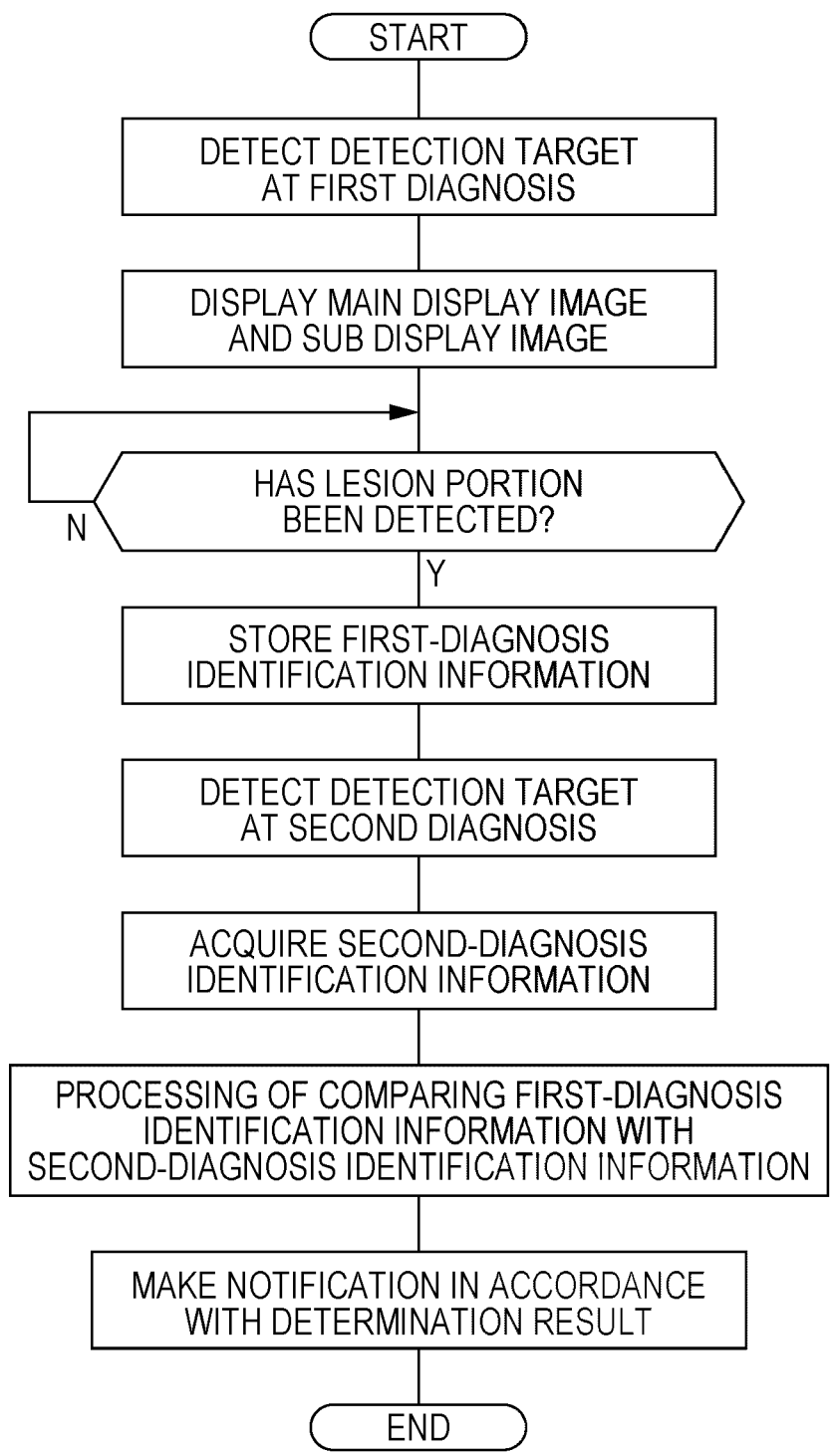
FIG. 11 is a flowchart illustrating a series of steps in a detection-target-oversight-prevention mode.

Next, a series of steps in the detection-target-oversight-prevention mode will be described with reference to the flowchart in FIG. 11. First, the detection-target-oversight-prevention mode is set, and the identification information switching unit 13e performs switching to "acquisition of first-diagnosis identification information". Subsequently, insertion of the distal end portion 12d of the endoscope 12 into a lumen is started, and the distal end portion 12d is gradually moved in a pressing direction in the lumen. To detect a detection target by moving the distal end portion 12d from the entrance of the lumen to the terminal of an observable range in the lumen is referred to as detection of a detection target at the first diagnosis.

In the detection-target-oversight-prevention mode, an observation target is alternately illuminated with normal light and special light. A main display image is generated from a Bc image signal, a Gc image signal, and an Rc image signal that are acquired during illumination with the normal light, and a sub display image is generated from a Bs image signal, a Gs image signal, and an Rs image signal that are acquired during illumination with the special light. The main display image and the sub display image are displayed on the monitor 18.

At the first diagnosis, an image feature value is detected from the image signals acquired during illumination with the special light, and whether or not the detected image feature value corresponds to the image feature value of a detection target is determined. If it is determined that the detected image feature value is the image feature value of a detection target (a detection target is detected), the detected image feature value and the position information at the point of time are stored as the first-diagnosis identification information in the identification information storage unit 72. Subsequently, when the distal end portion 12d of the endoscope 12 reaches the terminal position of the observable range of the lumen, the identification information switching unit 13e is operated to perform switching to "acquisition of second-diagnosis identification information". Subsequently, the distal end portion 12d is gradually moved in a pulling direction from the lumen to return along the same path as that of the first diagnosis. In this way, to detect a detection target by moving the distal end portion 12d from the terminal of the observable range of the lumen to the entrance of the lumen is referred to as detection of a detection target at the second diagnosis.

At the second diagnosis, an image feature value at the second diagnosis is detected from the image signals acquired during illumination with the special light, and the position information at the point of time is acquired as the second-diagnosis identification information. Every time the second-diagnosis identification information is acquired, the comparison processing unit 74 performs comparison processing of comparing the first-diagnosis identification information with the second-diagnosis identification information. In accordance with the result of the comparison processing, a determination "there is no oversight of a detection target", "there is an oversight of a detection target at the first diagnosis", or "there is an oversight of a detection target at the second diagnosis" is made. Subsequently, the notification control unit 76 makes a notification in accordance with the determination result. When a determination "there is an oversight of a detection target at the first diagnosis" or "there is an oversight of a detection target at the second diagnosis" is made, the notification control unit 76 makes a notification to make a user realize "an oversight of a detection target" by using a warning message or a warning sound.

In the above-described embodiment, when the comparison processing unit 74 performs image feature value comparison processing of comparing the image feature value at the first diagnosis with the image feature value at the second diagnosis, it is preferable to use, as an image feature value, a Gernika moment or Hu moment that is invariable with respect to a parallel shift, rotation, or scaling of an image, or SHIFT or SURF that is invariable with respect to a parallel shift, rotation, scaling, or change in illumination of an image.

Figure 12:
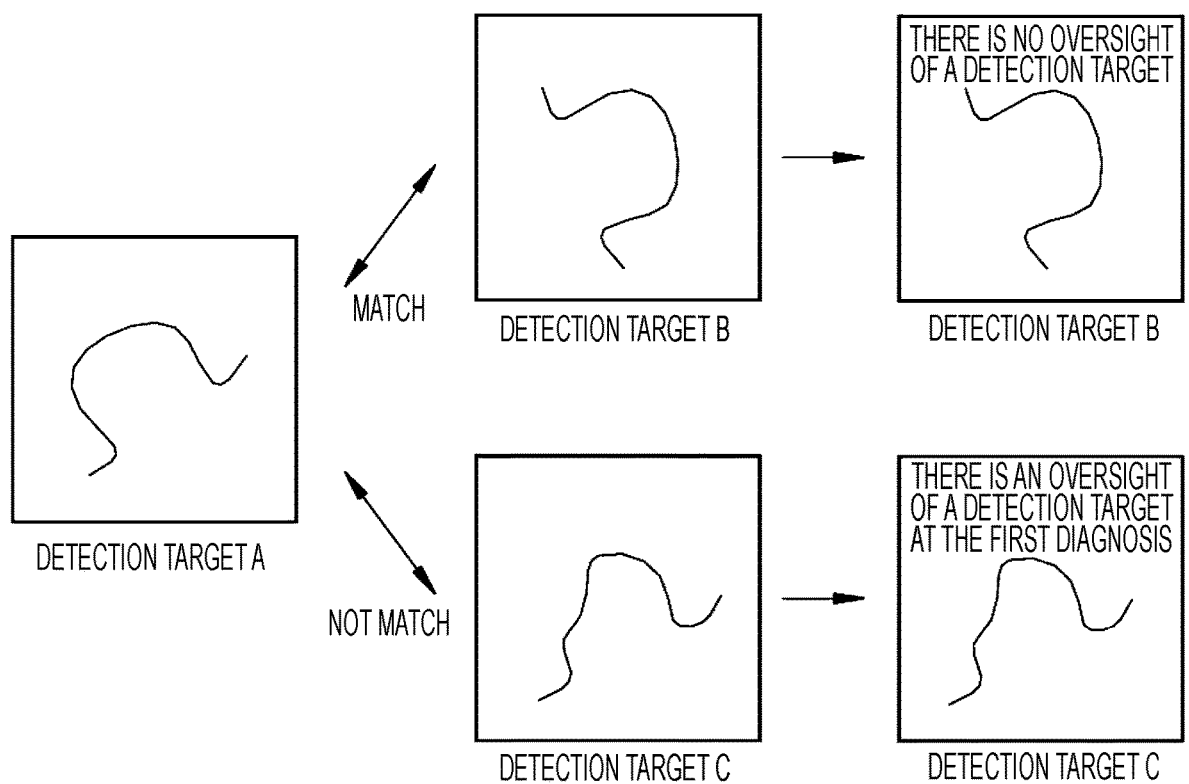
FIG. 12 is an explanatory diagram illustrating a case where detection targets match each other and a case where detection targets do not match each other in comparison processing.

As an example, the comparison processing unit 74 determines the degree of similarity on the basis of a matching method using Hu moments, and determines "an oversight of a detection target" on the basis of the determined degree of similarity. Here, as illustrated in FIG. 12, determination of the degree of similarity between the detection target A detected at the first diagnosis and the detection target B detected at the second diagnosis, and determination of the degree of similarity between the detection target A detected at the first diagnosis and the detection target C detected at the second diagnosis are illustrated. Preferably, the detection target includes not only the detection target itself but also a region including a normal portion around the detection target.

To determine the degree of similarity between the detection target A and the detection target B, a center moment in an image is calculated for each of the detection targets A and B by using the following equation (1).

$$\mu_{pq} = \sum_x \sum_y (x-\bar{x})^p (y-\bar{y})^q f(x,y) \qquad (1)$$

Here, x and y represent the coordinates of a pixel, and p, q=0, 1, 2, 3, and $$\bar{x} = \frac{m_{10}}{m_{00}}$$
$$\bar{y} = \frac{m_{01}}{m_{00}}$$

holds. However, $$m_{pq} = \sum_x \sum_y x^p y^q f(x,y)$$

holds.

Subsequently, a normalized center moment is calculated by using equation (2).

$$\eta_{pq} = \frac{\mu_{pq}}{\mu_{00}^\lambda} \qquad (2)$$

Here, $$\lambda = \frac{p+q}{2} + 1$$

holds. Finally, Hu moments, which are seven invariables, are calculated by using equation (3).

$$\begin{aligned}
h_1 &= \eta_{20} + \eta_{02} \\
h_2 &= (\eta_{20} - \eta_{02})^2 + 4\eta_{11} \\
h_3 &= (\eta_{30} - 3\eta_{12})^2 + (3\eta_{21} - \eta_{03})^2 \\
h_4 &= (\eta_{30} - \eta_{12})^2 + (\eta_{21} - \eta_{03})^2 \\
h_5 &= (\eta_{30} - 3\eta_{12})(\eta_{30} - \eta_{12})((\eta_{30} - \eta_{12})^2 - 3(\eta_{21} - \eta_{03})^2) + \\
&\quad (3\eta_{21} - \eta_{03})(\eta_{21} + \eta_{03})(3(\eta_{30} + \eta_{12})^2 - (\eta_{21} - \eta_{03})^2) \\
h_6 &= (\eta_{20} - \eta_{02})((\eta_{30} + \eta_{12})^2 - (\eta_{21} + \eta_{03})^2) + \\
&\quad 4\eta_{11}(\eta_{30} + \eta_{12})(\eta_{21} + \eta_{03}) \\
h_7 &= (3\eta_{21} - \eta_{03})(\eta_{30} + \eta_{12})((\eta_{30} + \eta_{12})^2 - 3(\eta_{21} - \eta_{03})^2) + \\
&\quad (3\eta_{12} - \eta_{03})(\eta_{21} + \eta_{03})(3(\eta_{30} + \eta_{12})^2 - (\eta_{21} - \eta_{03})^2)
\end{aligned} \qquad (3)$$

The Hu moments calculated for the detection target A and the detection target B are represented by $h_i^A$ and $h_j^B$, respectively. Finally, the degree of similarity between the detection target A and the detection target B is calculated by using equation (4).

$$I(A, B) = \sum_{i=1\ldots 7} |m_i^A - m_i^B| \qquad (4)$$

Here, $$m_i^A = \text{sign}(h_i^A) \cdot \log h_i^A$$

$$m_i^B = \text{sign}(h_i^B) \cdot \log h_i^B$$

holds. The following is a result of calculating the degree of similarity I(A, B) between the detection target A and the detection target B on the basis of the above.

$$I(A,B)=0.00001$$

Here, the degree of similarity increases as the value of the degree of similarity I decreases. Thus, if $$I(\alpha,\beta) \leq 0.000$$

is satisfied regarding the degree of similarity $I(\alpha,\beta)$ between the detection target $\alpha$ and the detection target $\beta$, the comparison processing unit 74 determines that the detection target $\alpha$ and the detection target $\beta$ are the same lesion (match). Thus, the degree of similarity I(A, B) between the detection target A and the detection target B is expressed by $$I(A,B)=0.0001 \leq 0.0001$$

and thus the comparison processing unit 74 determines that the detection target A and the detection target B are the same lesion and that there is no oversight of a detection target at the first diagnosis. In this case, a determination "there is no oversight of a detection target" is made, and the fact is displayed on the monitor 18.

Subsequently, to determine the degree of similarity between the detection target A and the detection target C, the degree of similarity I(A, C) is calculated in accordance with a procedure similar to that for determining the degree of similarity between the detection targets A and B. As a result of calculating the degree of similarity I(A, C), $$I(A,C)=0.04677 > 0.0001$$

is obtained, and thus it is determined that the detection target A and the detection target C are lesions different from each other and that the detection target C is overlooked at the first diagnosis. In this case, a determination "there is an oversight of a detection target at the first diagnosis" is displayed on the monitor 18.

Figure 13:
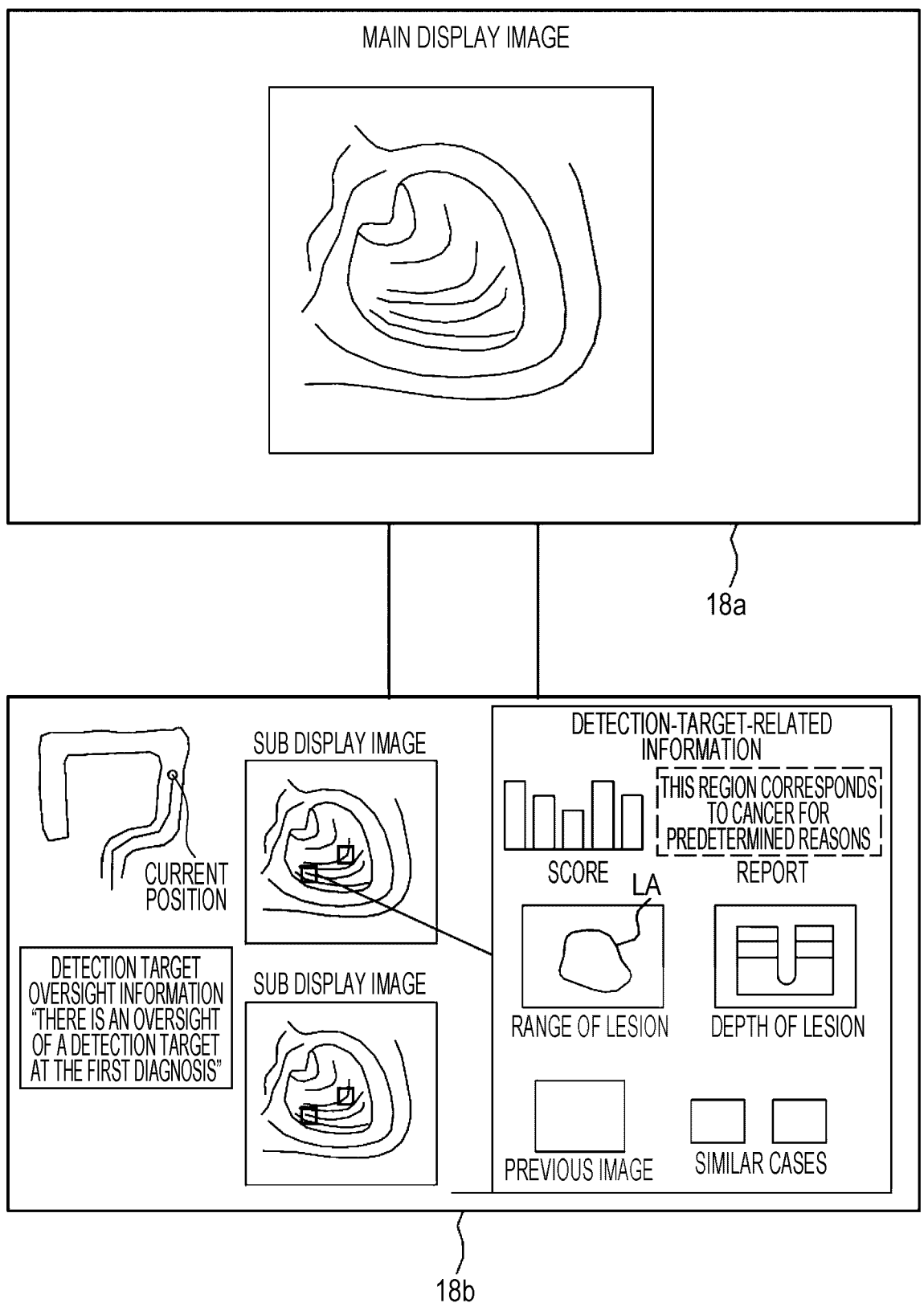
FIG. 13 is an image diagram of a monitor that displays a main display image and a monitor that displays sub display images and detection-target-related information.

In the above-described embodiment, a main display image and sub display images are displayed side by side on the single monitor 18. Alternatively, the main display image and the sub display images may be displayed by using a plurality of monitors 18. Specifically, it is preferable to display the main display image on one of the plurality of monitors 18 and to display the sub display images on the other monitors. For example, in the case of using two monitors: a monitor 18a and a monitor 18b, as illustrated in FIG. 13, only the main display image is displayed on the entire screen of the monitor 18a, whereas only the sub display images and information related to a detection target are displayed on the monitor 18b. The monitor 18a and the monitor 18b may be coupled to each other by a coupling arm or the like.

Figure 14:
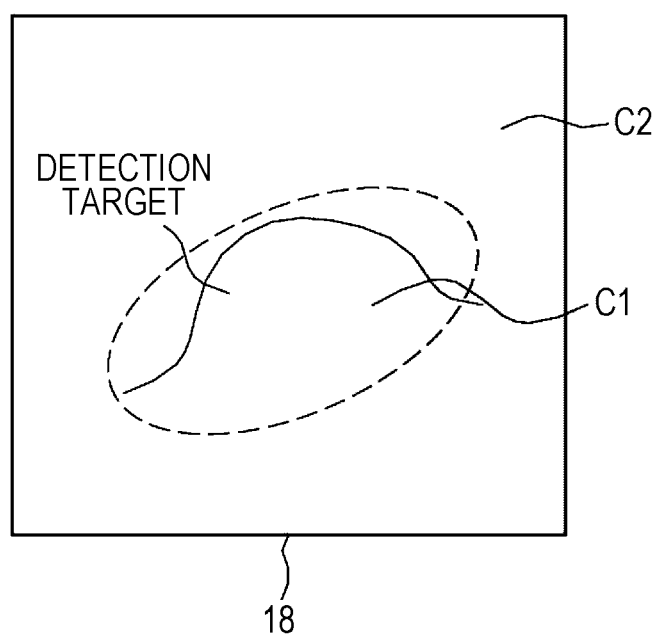
FIG. 14 is an image diagram of a detection target to which color is assigned in accordance with a lesion score and the surroundings thereof.

In the above-described embodiment, a notification is made by using an indicator or the like when a detection target is detected. In addition to this, the entire image including a detection target (the entire main display image or the entire sub display image) may be evaluated in terms of a probability of being a lesion region by using a lesion score, and the lesion score may be assigned to a color map and displayed. For example, in the case of FIG. 14, a color C1 (for example, red) of a detection target and the surroundings thereof and a color C2 (for example, blue) of a region away from the detection target are quite different from each other.

In the above-described embodiment, when the lesion determination unit 70c determines that the detected image feature value is the image feature value of a detection target (hereinafter "when a detection target is detected"), the detection target may be automatically magnified by using electronic zoom or optical zoom by the magnifying optical system 36. When a detection target is detected, display for prompting a user to magnify the detection target by using optical zoom may be performed. Preferably, the magnified detection target is displayed as a main display image or a sub display image.

In the above-described embodiment, when a detection target is detected, a still image may be automatically stored. In the case of automatically storing a still image, it is preferable to acquire images of a plurality of frames as candidate still images to be stored, and to store, as a still image, the most tightly focused image among the candidate still images of the plurality of frames. A method for selecting a tightly focused image is, for example, to perform frequency analysis on the individual candidate still images to be stored and to select an image including a largest amount of high-frequency components as a still image to be stored.

In the above-described embodiment, a case is assumed where the distal end portion 12d of the endoscope 12 is caused to go and return in a lumen of the stomach, large intestine, esophagus, or the like in one diagnosis of a lesion, in which the former half corresponds to the first diagnosis and the latter half for returning the same path as the former half corresponds to the second diagnosis. The first diagnosis and the second diagnosis are not limited to the former half and the latter half of one diagnosis of a lesion, and another case may also be applied as long as the second diagnosis is performed after the first diagnosis in terms of time, and as long as the first diagnosis and the second diagnosis are performed along the same path to detect a lesion. For example, the first diagnosis and the second diagnosis may be performed on different dates to diagnose a lesion. In this case, the date of a first diagnosis, such as an initial diagnosis, may correspond to the time of the first diagnosis, and the date of a second diagnosis, such as follow-up, after the date of the first diagnosis may correspond to the time of the second diagnosis. In this case, it is preferable to automatically switch from "acquisition of first-diagnosis identification information" to "acquisition of second-diagnosis identification information" without operating the identification information switching unit 13e.

In the above-described embodiment, whether or not there is an oversight of a detection target at the first diagnosis and the second diagnosis is determined by using both position information and an image feature value. Alternatively, whether or not there is an oversight of a detection target may be determined by using only an image feature value. In this case, comparison processing of comparing an image feature value of a detection target at the first diagnosis with an image feature value of a detection target at the second diagnosis is performed, and whether or not there is an oversight of a detection target is determined in accordance with the result of the comparison processing.

Second Embodiment

In a second embodiment, an observation target is illuminated by using a laser light source and a fluorescent body instead of the LEDs 20a to 20d of four colors according to the above-described first embodiment. Hereinafter, a description will be given of only a part different from that of the first embodiment, and a description will not be given of a part substantially the same as that of the first embodiment.

Figure 15:
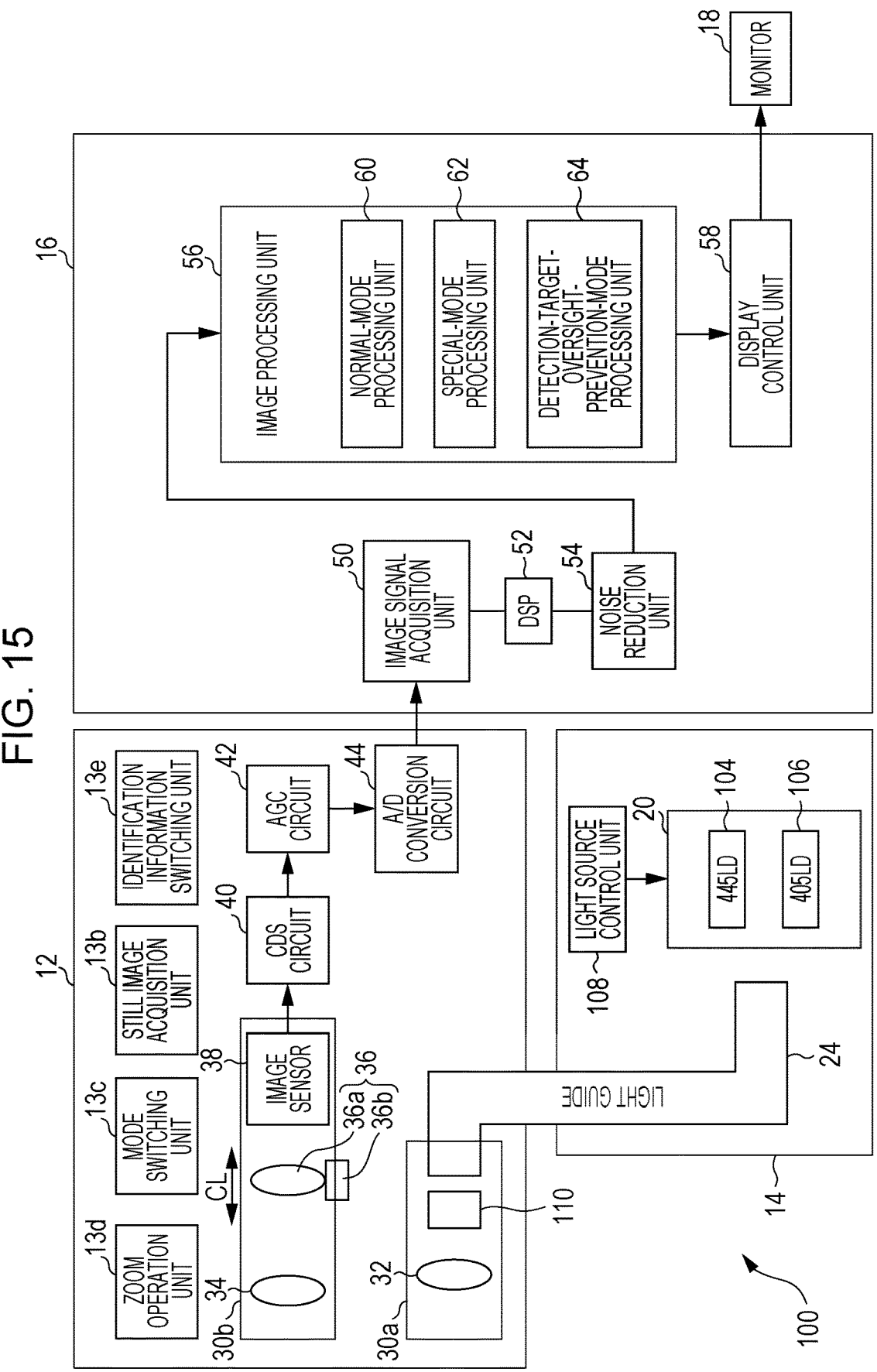
FIG. 15 is a block diagram illustrating the functions of an endoscope system according to a second embodiment.

As illustrated in FIG. 15, in an endoscope system 100 according to the second embodiment, the light source unit 20 of the light source device 14 is provided with, instead of the LEDs 20a to 20d of four colors, a blue laser light source (referred to as "445LD", LD stands for "laser diode") 104 that emits blue laser light having a center wavelength of 445±10 nm and a blue-violet laser light source (referred to as "405LD") 106 that emits blue-violet laser light having a center wavelength of 405±10 nm. The light emission from semiconductor light emitting elements of the light sources 104 and 106 is individually controlled by a light source control unit 108, and the light amount ratio between the light emitted by the blue laser light source 104 and the light emitted by the blue-violet laser light source 106 is freely changed.

In the normal mode, the light source control unit 108 turns on the blue laser light source 104. On the other hand, in the special mode, the light source control unit 108 turns on both the blue laser light source 104 and the blue-violet laser light source 106 and performs control so that the light emission rate of blue laser light is higher than the light emission rate of blue-violet laser light. In the detection-target-oversight-prevention mode, the light source control unit 108 alternately performs control to turn on only the blue laser light source 104 and control to turn on both the blue laser light source 104 and the blue-violet laser light source 106.

Preferably, the half-width of the blue laser light or the blue-violet laser light is about ±10 nm. As the blue laser light source 104 and the blue-violet laser light source 106, an InGaN-based laser diode of a broad area type can be used, and also an InGaNAs-based laser diode or a GaNAs-based laser diode can be used. Alternatively, a configuration using a light emitting body, such as a light emitting diode, may be used as the above-described light sources.

The illumination optical system 30a is provided with a fluorescent body 110 that the blue laser light or the blue-violet laser light from the light guide 24 enters, in addition to the illumination lens 32. The fluorescent body 110 is excited by the blue laser light and emits fluorescence. Part of the blue laser light passes through the fluorescent body 110 without exciting the fluorescent body 110. The blue-violet laser light passes through the fluorescent body 110 without exciting the fluorescent body 110. The light from the fluorescent body 110 illuminates the inside of the body of an observation target through the illumination lens 32.

Figure 16:
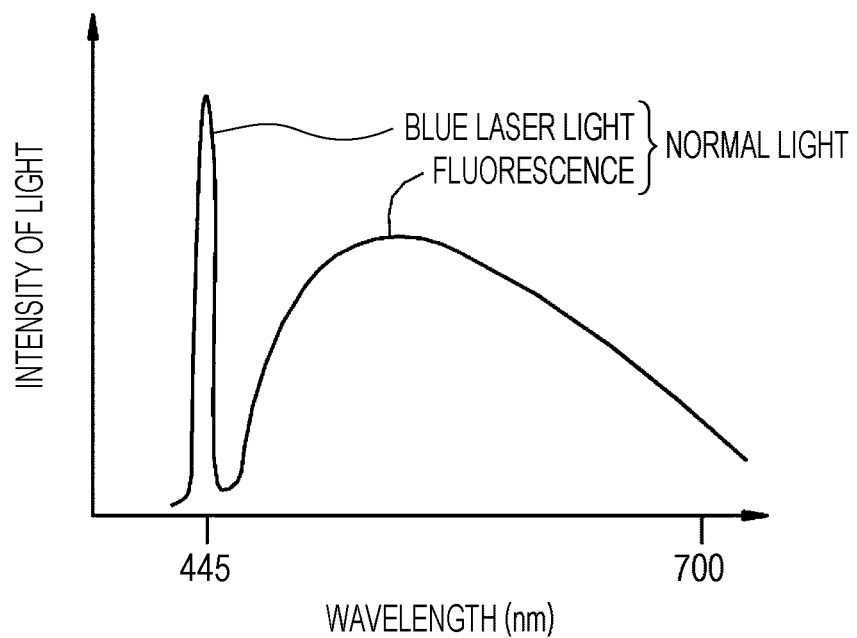
FIG. 16 is a graph illustrating a spectrum of normal light according to the second embodiment.

Here, in the normal mode, the blue laser light mainly enters the fluorescent body 110. Thus, wide-range light for the normal mode, generated by combining the blue laser light and fluorescence emitted by the fluorescent body 110 as a result of excitation caused by the blue laser light, as illustrated in FIG. 16, is applied as normal light to an observation target. The image sensor 38 performs imaging of the observation target illuminated with the normal light, and accordingly a normal image composed of a Bc image signal, a Gc image signal, and an Rc image signal is acquired.

Figure 17:
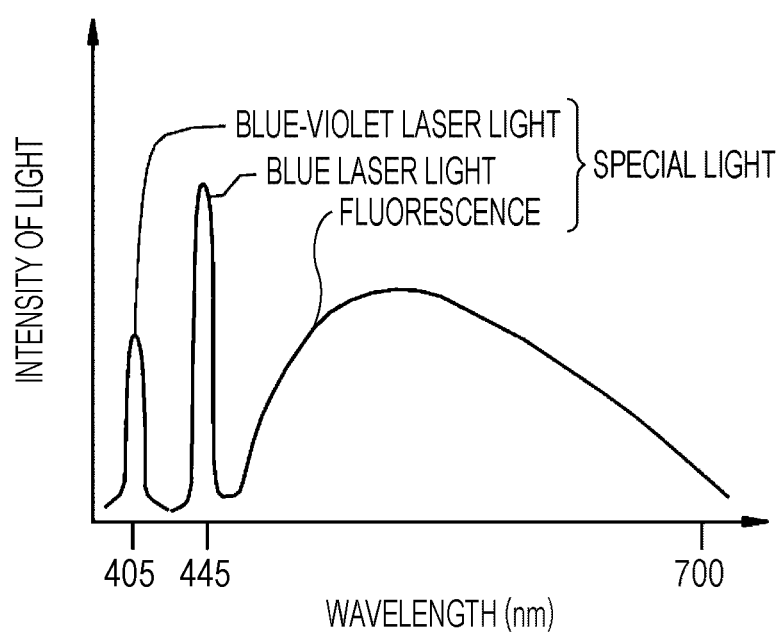
FIG. 17 is a graph illustrating a spectrum of special light according to the second embodiment.

On the other hand, in the special mode, both the blue-violet laser light and the blue laser light enter the fluorescent body 110. Thus, wide-range light for the special mode, generated by combining the blue-violet laser light, the blue laser light, and fluorescence emitted by the fluorescent body 110 as a result of excitation caused by the blue laser light, as illustrated in FIG. 17, is applied as special light to an observation target. The image sensor 38 performs imaging of the observation target illuminated with the special light, and accordingly a special image composed of a Bs image signal, a Gs image signal, and an Rs image signal is acquired.

In the detection-target-oversight-prevention mode, the normal light illustrated in FIG. 16 and the special light illustrated in FIG. 17 are alternately applied to an observation target. A main display image is generated from the Bc image signal, Gc image signal, and Rc image signal that are acquired during illumination with the normal light, and a sub display image is generated from the Bs image signal, Gs image signal, and Rs image signal that are acquired during illumination with the special light. In addition, identification information of a detection target is detected from the Bs image signal, Gs image signal, and Rs image signal that are acquired during illumination with the special light.

Preferably, the fluorescent body 110 is made of a plurality of types of fluorescent materials that absorb part of the blue laser light and emit green to yellow light as a result of excitation (for example, a YAG-based fluorescent body, a $BaMgAl_{10}O_{17}$ (BAM)-based fluorescent body, or the like). As in this configuration example, when a semiconductor light emitting element is used as an excitation light source of the fluorescent body 110, high-intensity white light can be acquired at high emission efficiency, the intensity of the white light can be easily adjusted, and the change in color temperature and chromaticity of the white light can be reduced.

Third Embodiment

In a third embodiment, an observation target is illuminated by using a white light source, such as a xenon lamp, and a rotational filter, instead of the LEDs 20a to 20d of four colors. Imaging of the observation target may be performed by using a monochrome image sensor instead of the color image sensor 38. Hereinafter, a description will be given of only a part different from that of the first embodiment, and a description will not be given of a part substantially the same as that of the first embodiment.

Figure 18:
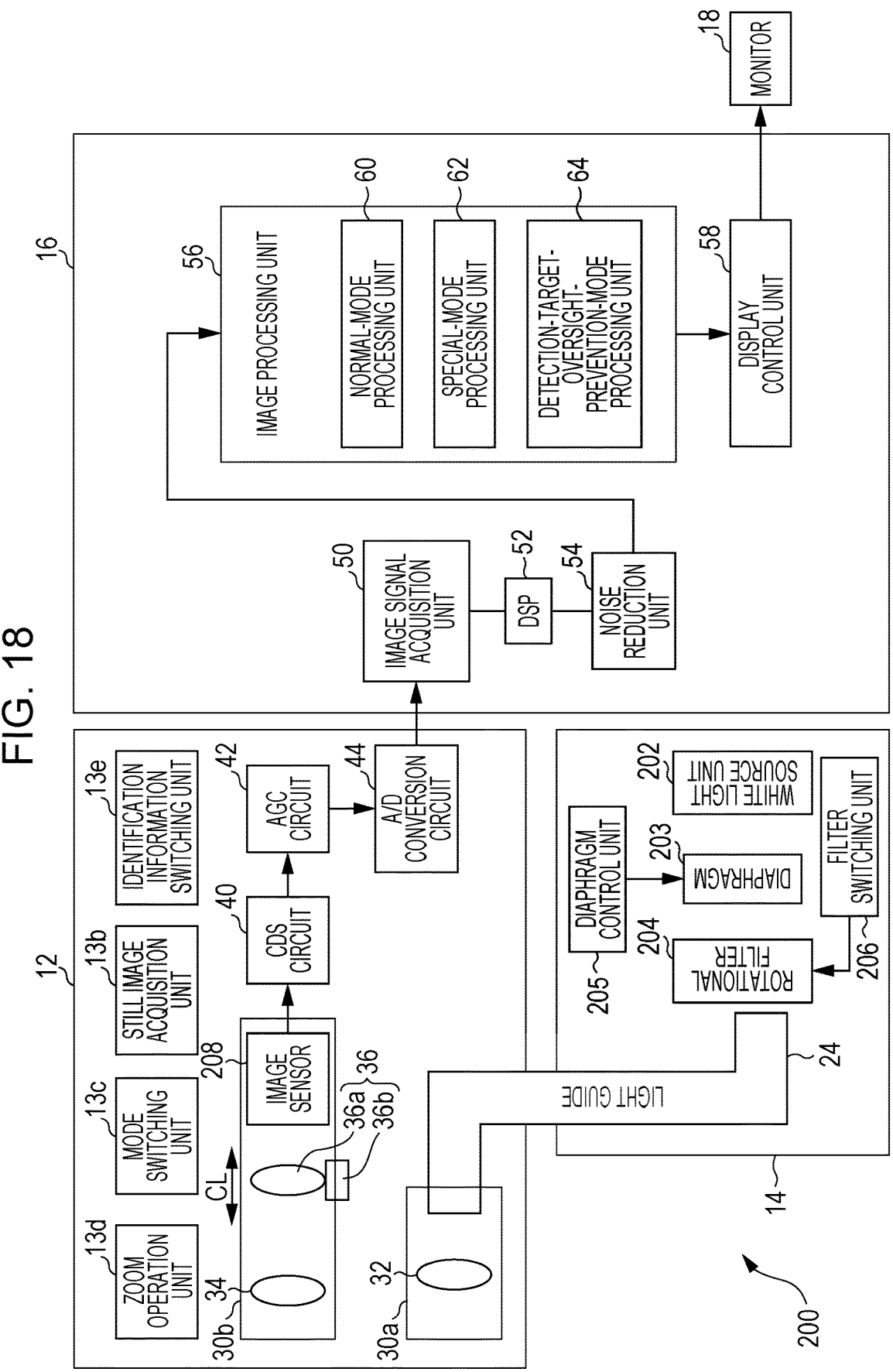
FIG. 18 is a block diagram illustrating the functions of an endoscope system according to a third embodiment.

In an endoscope system 200 illustrated in FIG. 18, the light source device 14 is provided with a white light source unit 202, a rotational filter 204, and a filter switching unit 206, instead of the LEDs 20a to 20d in the endoscope system 10. The imaging optical system 30b is provided with a monochrome image sensor 208 that is not provided with color filters, instead of the color image sensor 38. A diaphragm 203 is provided between the white light source unit 202 and the rotational filter 204. The area of the opening portion of the diaphragm 203 is adjusted by a diaphragm control unit 205.

The white light source unit 202 is a xenon lamp, a white LED, or the like, and emits white light having a wavelength range from blue to red. The rotational filter 204 includes a normal-mode filter 210 provided on the inner side closest to a rotational axis, and a special-mode filter 212 and a detection-target-oversight-prevention-mode filter 214 that are provided on the outer side of the normal-mode filter 210 (see FIG. 19).

The filter switching unit 206 moves the rotational filter 204 in a diameter direction. Specifically, when the normal mode is set by the mode switching unit 13c, the filter switching unit 206 inserts the normal-mode filter 210 into the light path of white light. When the special mode is set, the filter switching unit 206 inserts the special-mode filter 212 into the light path of white light. When the detection-target-oversight-prevention mode is set, the filter switching unit 206 inserts the detection-target-oversight-prevention-mode filter 214 into the light path of white light.

Figure 19:
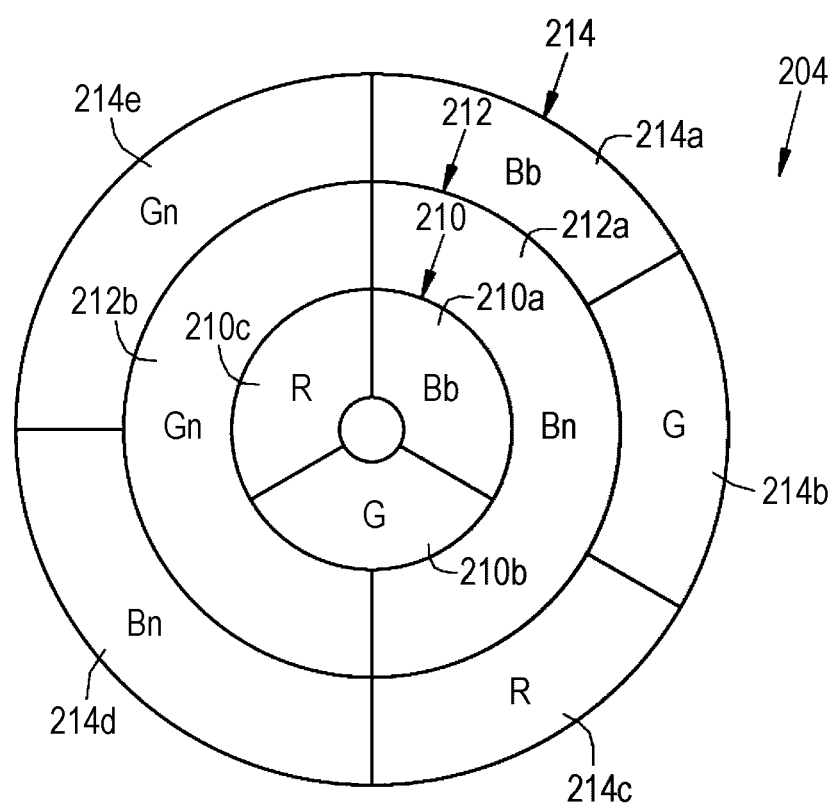
FIG. 19 is a plan view of a rotational filter.

As illustrated in FIG. 19, the normal-mode filter 210 is provided with a Bb filter 210a, a G filter 210b, and an R filter 210c in a circumferential direction. The Bb filter 210a passes wide-range blue light Bb having a wavelength range of 400 to 500 nm of white light. The G filter 210b passes green light G of white light. The R filter 210c passes red light R of white light. Thus, in the normal mode, rotation of the rotational filter 204 causes the wide-range blue light Bb, the green light G, and the red light R to be sequentially emitted as normal light toward an observation target.

The special-mode filter 212 is provided with a Bn filter 212a and a Gn filter 212b in the circumferential direction. The Bn filter 212a passes blue narrow-range light Bn in 400 to 450 nm of white light. The Gn filter 212b passes green narrow-range light Gn in 530 to 570 nm of white light. Thus, in the special mode, rotation of the rotational filter 204 causes the blue narrow-range light and the green narrow-range light to be sequentially emitted as special light toward an observation target.

The detection-target-oversight-prevention-mode filter 214 is provided with a Bb filter 214a, a G filter 214b, an R filter 214c, a Bn filter 214d, and a Gn filter 214e in the circumferential direction. The Bb filter 214a passes the wide-range blue light Bb of white light. The G filter 214b passes the green light G of white light. The R filter 214c passes the red light R of white light. The Bn filter 214d passes the blue narrow-range light Bn of white light. The Gn filter 214e passes the green narrow-range light Gn of white light. Thus, in the detection-target-oversight-prevention mode, rotation of the rotational filter 204 causes the wide-range blue light Bb, the green light G, and the red light R to be sequentially emitted as normal light toward an observation target, and the blue narrow-range light and the green narrow-range light to be sequentially emitted as special light toward the observation target.

In the endoscope system 200, in the normal mode, imaging of an observation target is performed by the monochrome image sensor 208 every time the observation target is illuminated with the wide-range blue light Bb, the green light G, and the red light R. Accordingly, a Bc image signal is acquired during illumination with the wide-range blue light Bb, a Gc image signal is acquired during illumination with the green light G, and an Rc image signal is acquired during illumination with the red light R. The Bc image signal, the Gc image signal, and the Rc image signal constitute a normal image.

In the special mode, imaging of an observation target is performed by the monochrome image sensor 208 every time the observation target is illuminated with the blue narrow-range light Bn and the green narrow-range light Gn. Accordingly, a Bn image signal is acquired during illumination with the blue narrow-range light Bn, and a Gn image signal is acquired during illumination with the green narrow-range light Gn. The Bn image signal and the Gn image signal constitute a special image.

In the detection-target-oversight-prevention mode, a main display image is generated on the basis of the Bc image signal acquired during illumination with the wide-range blue light Bb, the Gc image signal acquired during illumination with the green light G, and the Rc image signal acquired during illumination with the red light R. In addition, a sub display image is generated on the basis of the Bn image signal acquired during illumination with the blue narrow-range light Bn and the Gn image signal acquired during illumination with the green narrow-range light Gn, and a detection target is detected from the Bn image signal and the Gn image signal.

In the above-described embodiments, the hardware structure of a processing unit that executes various processing operations, such as the image processing unit 56, may be various processors described below. The various processors include a central processing unit (CPU), which is a general-purpose processor executing software (program) and functioning as various processing units; a programmable logic device (PLD), which is a processor whose circuit configuration is changeable after manufacturing, such as a field programmable gate array (FPGA); a dedicated electric circuit, which is a processor having a circuit configuration designed exclusively for executing various processing operations, and the like.

A single processing unit may be constituted by one of these various processors or may be constituted by a combination of two or more processors of the same type or different types (for example, a combination of a plurality of FPGAs or a combination of a CPU and an FPGA). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various processing units are constituted by using one or more of the above-described various processors as a hardware structure.

Furthermore, the hardware structure of these various processors is, more specifically, electric circuitry including a combination of circuit elements, such as semiconductor elements.

REFERENCE SIGNS LIST 10 endoscope system
12 endoscope
12a insertion section
12b operation section
12c bending portion
12d distal end portion
13a angle knob
13b still image acquisition unit
13c mode switching unit
13d zoom operation unit
13e identification information switching unit
14 light source device
16 processor device
18, 18a, 18b monitor
19 console
20 light source unit
20a V-LED (light source)
20b B-LED (light source)
20c G-LED (light source)
20d R-LED (light source)
22 light source control unit
23 wavelength cut filter
24 light guide
30a illumination optical system
30b imaging optical system
32 illumination lens
34 objective lens
36 magnifying optical system
36a zoom lens
36b lens driving unit
38 image sensor
40 CDS circuit
42 AGC circuit
44 A/D conversion circuit
48 graduation detection sensor
50 image signal acquisition unit
52 DSP
54 noise reduction unit
56 image processing unit
58 display control unit
60 normal-mode processing unit
62 special-mode processing unit
64 detection-target-oversight-prevention-mode processing unit
70 identification information acquisition unit
70a position information calculation unit
70b image feature value detection unit
70c lesion determination unit
72 identification information storage unit
74 comparison processing unit
76 notification control unit
100 endoscope system
104 blue laser light source
106 blue-violet laser light source
108 light source control unit
110 fluorescent body
200 endoscopy system
202 white light source
204 rotational filter
205 diaphragm control unit
206 filter switching unit
208 image sensor
210 normal-mode filter
210a Bb filter
210b G filter
210c R filter
212 special-mode filter
212a Bn filter
212b Gn filter
214 detection-target-oversight-prevention-mode filter
214a Bb filter
214b G filter
214c R filter
214d Bn filter
214e Gn filter

What is claimed is:

1. An endoscope system comprising:
a processor configured to function as:
an identification information acquisition unit that acquires first-diagnosis identification information at a first diagnosis and acquires second-diagnosis identification information at a second diagnosis that is different from the first diagnosis,
wherein the first-diagnosis identification information includes an image feature value of a detection target at the first diagnosis detected from an image acquired at the first diagnosis, and the second-diagnosis identification information includes an image feature value of a detection target at the second diagnosis detected from an image acquired at the second diagnosis;
a comparison processing unit that performs comparison processing of comparing the first-diagnosis identification information with the second-diagnosis identification information; and
a notification unit that makes, if a determination is made as a result of the comparison processing that there is a difference in a detection target between the first diagnosis and the second diagnosis due to a phenomenon that the detection target is not photographed in either the image acquired at the first diagnosis or the image acquired at the second diagnosis, a notification about an oversight of the detection target.

2. The endoscope system according to claim 1, wherein the processor is further configured to function as an image feature value detection unit that automatically detects the image feature value of the detection target at the first diagnosis and automatically detects the image feature value of the detection target at the second diagnosis.

3. The endoscope system according to claim 1, wherein the notification unit makes the notification about the oversight of the detection target if a determination is made that the image feature value of the detection target at the first diagnosis does not match the image feature value of the detection target at the second diagnosis as a result of the comparison processing.

4. The endoscope system according to claim 2, wherein the notification unit makes the notification about the oversight of the detection target if a determination is made that the image feature value of the detection target at the first diagnosis does not match the image feature value of the detection target at the second diagnosis as a result of the comparison processing.

5. The endoscope system according to claim 1, wherein the first-diagnosis identification information further includes position information at the first diagnosis, the second-diagnosis identification information further includes position information at the second diagnosis, and the notification unit makes the notification about the oversight of the detection target if a determination is made that the position information at the first diagnosis matches the position information at the second diagnosis and that the image feature value of the detection target at the first diagnosis does not match the image feature value of the detection target at the second diagnosis as a result of the comparison processing.

6. The endoscope system according to claim 2, wherein the first-diagnosis identification information further includes position information at the first diagnosis, the second-diagnosis identification information further includes position information at the second diagnosis, and the notification unit makes the notification about the oversight of the detection target if a determination is made that the position information at the first diagnosis matches the position information at the second diagnosis and that the image feature value of the detection target at the first diagnosis does not match the image feature value of the detection target at the second diagnosis as a result of the comparison processing.

7. The endoscope system according to claim 5, wherein the notification unit makes the notification about the oversight of the detection target if a determination is made that position information at the first diagnosis does not match position information at the second diagnosis and that an image feature value of a detection target at the first diagnosis does not match an image feature value of the detection target at the second diagnosis as a result of the comparison processing.

8. The endoscope system according to claim 6, wherein the notification unit makes the notification about the oversight of the detection target if a determination is made that position information at the first diagnosis does not match position information at the second diagnosis and that an image feature value of a detection target at the first diagnosis does not match an image feature value of the detection target at the second diagnosis as a result of the comparison processing.

9. The endoscope system according to claim 1, wherein the processor is further configured to function as an identification information switching unit that switches acquisition of identification information by the identification information acquisition unit from acquisition of the first-diagnosis identification information to acquisition of the second-diagnosis identification information.

10. The endoscope system according to claim 2, wherein the processor is further configured to function as an identification information switching unit that switches acquisition of identification information by the identification information acquisition unit from acquisition of the first-diagnosis identification information to acquisition of the second-diagnosis identification information.

11. The endoscope system according to claim 3, wherein the processor is further configured to function as an identification information switching unit that switches acquisition of identification information by the identification information acquisition unit from acquisition of the first-diagnosis identification information to acquisition of the second-diagnosis identification information.

12. The endoscope system according to claim 4, wherein the processor is further configured to function as an identification information switching unit that switches acquisition of identification information by the identification information acquisition unit from acquisition of the first-diagnosis identification information to acquisition of the second-diagnosis identification information.

13. The endoscope system according to claim 5, wherein the processor is further configured to function as an identification information switching unit that switches acquisition of identification information by the identification information acquisition unit from acquisition of the first-diagnosis identification information to acquisition of the second-diagnosis identification information.

14. The endoscope system according to claim 1, wherein the notification unit includes a monitor and makes the notification by displaying a warning message on the monitor.

15. The endoscope system according to claim 2, wherein the notification unit includes a monitor and makes the notification by displaying a warning message on the monitor.

16. The endoscope system according to claim 3, wherein the notification unit includes a monitor and makes the notification by displaying a warning message on the monitor.

17. The endoscope system according to claim 1, wherein the notification unit includes a speaker and makes the notification by outputting a warning sound from the speaker.

18. The endoscope system according to claim 2, comprising:
a plurality of light sources having different wavelength characteristics, wherein
the image feature value detection unit detects, from an image acquired by using at least one of the plurality of light sources, the image feature value of the detection target at the first diagnosis or the image feature value of the detection target at the second diagnosis.

19. The endoscope system according to claim 1, wherein the first diagnosis is a diagnosis performed by moving a distal end portion of an endoscope from an entrance of a lumen to a terminal of an observable range in the lumen, and the second diagnosis is a diagnosis performed by moving the distal end portion of the endoscope from the terminal of the observable range of the lumen by the first diagnosis to the entrance of the lumen.

20. An operation method for an endoscope system, comprising:
acquiring first-diagnosis identification information at a first diagnosis and second-diagnosis identification information at a second diagnosis that is different from the first diagnosis, wherein the first-diagnosis identification information includes an image feature value of a detection target at the first diagnosis detected from an image acquired at the first diagnosis, and the second-diagnosis identification information includes an image feature value of a detection target at the second diagnosis detected from an image acquired at the second diagnosis;

performing comparison processing of comparing the first-diagnosis identification information with the second-diagnosis identification information; and making if a determination is made as a result of the comparison processing that there is a difference in a detection target between the first diagnosis and the second diagnosis due to a phenomenon that the detection target is not photographed in either the image acquired at the first diagnosis or the image acquired at the second diagnosis, a notification about an oversight of the detection target.

* * * * *